(12) United States Patent
Otake et al.

(10) Patent No.: US 10,520,564 B2
(45) Date of Patent: Dec. 31, 2019

(54) HIGH FREQUENCY COIL AND MAGNETIC RESONANCE IMAGING DEVICE

(71) Applicant: Hitachi, Ltd., Chiyoda-ku, Tokyo (JP)

(72) Inventors: Yosuke Otake, Tokyo (JP); Hisaaki Ochi, Tokyo (JP); Kohjiro Iwasawa, Tokyo (JP)

(73) Assignee: Hitachi, Ltd., Tokyo (JP)

(*) Notice: Subject to any disclaimer, the term of this patent is extended or adjusted under 35 U.S.C. 154(b) by 90 days.

(21) Appl. No.: 15/736,224

(22) PCT Filed: Aug. 22, 2016

(86) PCT No.: PCT/JP2016/074374
§ 371 (c)(1),
(2) Date: Dec. 13, 2017

(87) PCT Pub. No.: WO2017/033887
PCT Pub. Date: Mar. 2, 2017

(65) Prior Publication Data
US 2018/0180690 A1      Jun. 28, 2018

(30) Foreign Application Priority Data

Aug. 27, 2015 (JP) .................... 2015-167727

(51) Int. Cl.
*G01R 33/3415* (2006.01)
*A61B 5/055* (2006.01)
(Continued)

(52) U.S. Cl.
CPC .......... *G01R 33/3415* (2013.01); *A61B 5/055* (2013.01); *A61B 5/0555* (2013.01);
(Continued)

(58) Field of Classification Search
CPC .................. A61B 5/055; A61B 5/0555; G01R 33/34053; G01R 33/34069;
(Continued)

(56) References Cited

U.S. PATENT DOCUMENTS 5,153,517 A    10/1992  Oppelt et al.
5,500,594 A     3/1996  Leussler
(Continued)

FOREIGN PATENT DOCUMENTS

JP    3-23842 A    1/1991
JP    3-188828 A   8/1991
(Continued)

OTHER PUBLICATIONS

Notification of Transmittal of Translation of the International Preliminary Report on Patentability (PCT/IB/338 &PCT/IB/373) issued in PCT Application No. PCT/JP2016/074374 dated Mar. 8, 2018, including English translation (Japanese-language Written Opinion (PCT/ISA/237) previously filed on Dec. 13, 2017 (five (5) pages).
(Continued)

*Primary Examiner* — Rishi R Patel
(74) *Attorney, Agent, or Firm* — Crowell & Moring LLP

(57) ABSTRACT

In a multi-channel array coil used as an RF coil of an MRI apparatus, even when magnetic coupling occurs between the respective sub-coils, it is possible to suppress the influence of a current flowing through the sub-coil of a coupling counterpart to maintain the desired sensitivity and suppress deterioration of image quality. Therefor, even when magnetic coupling occurs between sub-coils constituting the multi-channel array coil used as the RF coil of the MRI apparatus, the sub-coils are connected to a signal processing circuit so that a phase difference between a rotating magnetic field generated by the influence of a current flowing through the sub-coil of the coupling counterpart and a rotating
(Continued)

magnetic field generated by the sub-coil is less than 90 degrees.

11 Claims, 22 Drawing Sheets

(51) Int. Cl.
 *G01R 33/36* (2006.01)
 *G01R 33/34* (2006.01)
(52) U.S. Cl.
 CPC ...... *G01R 33/365* (2013.01); *G01R 33/34053* (2013.01); *G01R 33/34069* (2013.01)
(58) Field of Classification Search
 CPC .............. G01R 33/3415; G01R 33/365; G01R 33/3642; G01R 33/36
 See application file for complete search history.

(56) References Cited

U.S. PATENT DOCUMENTS

2009/0021256 A1* 1/2009 Soutome .......... G01R 33/34007
 324/318
2011/0115483 A1 5/2011 Zhai et al.
2013/0314091 A1 11/2013 Otake et al.

FOREIGN PATENT DOCUMENTS

| JP | 6-54824 A | 3/1994 |
| JP | 7-265278 A | 10/1995 |
| JP | 10-52416 A | 2/1998 |
| JP | 2004-81514 A | 3/2004 |
| JP | 2011-505955 A | 3/2011 |
| WO | WO 2012/111433 A1 | 8/2012 |

OTHER PUBLICATIONS

International Search Report (PCT/ISA/210) issued in PCT Application No. PCT/JP2016/074374 dated Nov. 15, 2016 with English translation (5 pages).
Japanese-language Written Opinion (PCT/ISA/237) issued in PCT Application No. PCT/JP2016/074374 dated Nov. 15, 2016 (3 pages).
Roemer et al., "The NMR Phased Array", Magnetic Resonance in Medicine, 1990, pp. 192-225, vol. 16.
Pruessmann et al. "SENSE: Sensitivity Encoding for Fast MRI", Magnetic Resonance in Medicine, 1999, pp. 952-962, vol. 42.

* cited by examiner

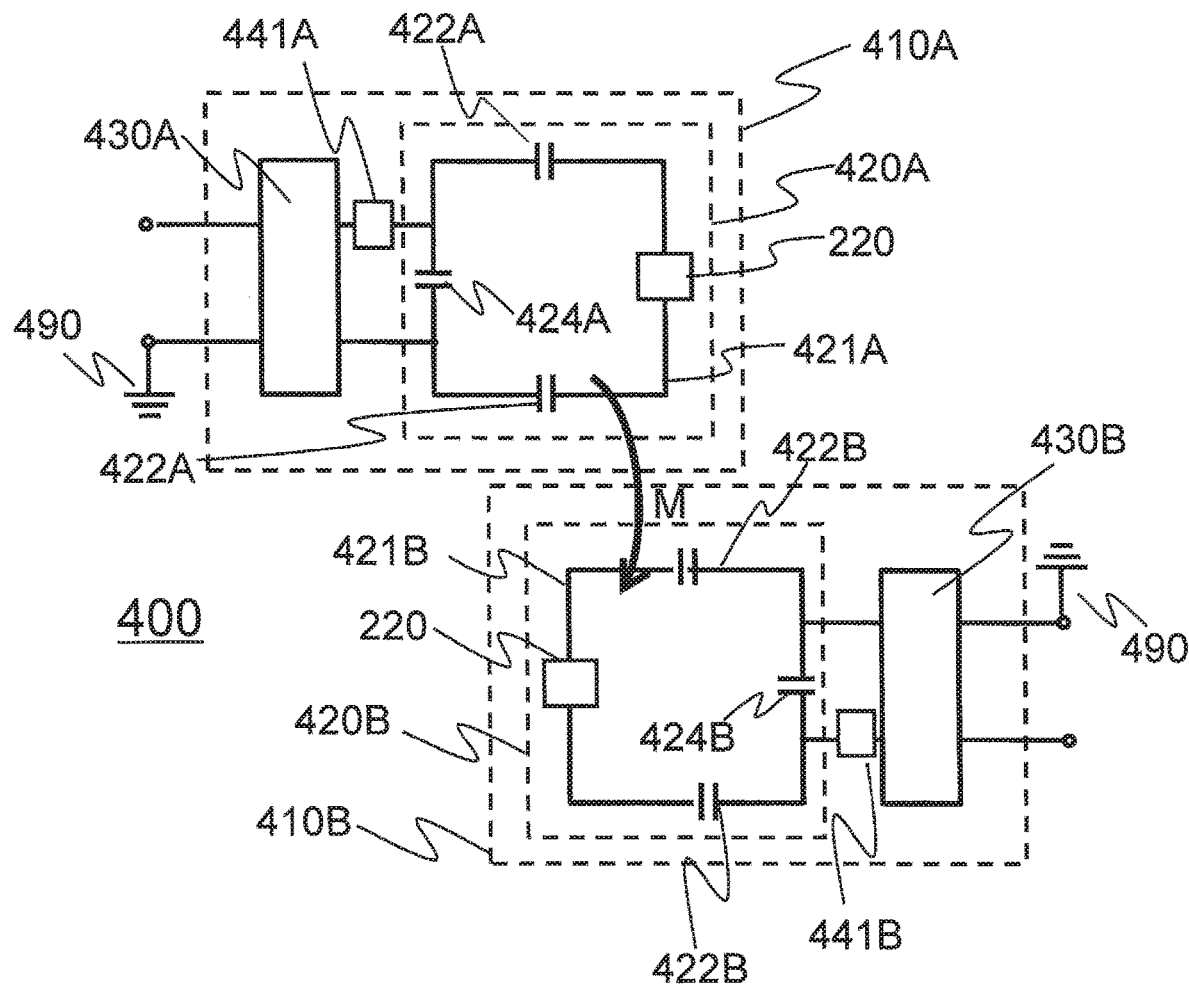
FIG. 5A
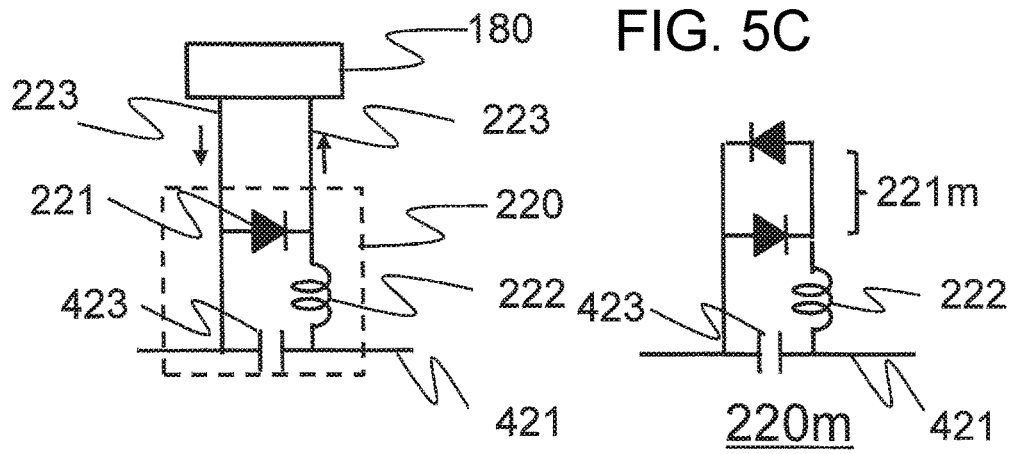
FIG. 5B
FIG. 5C

HIGH FREQUENCY COIL AND MAGNETIC RESONANCE IMAGING DEVICE

TECHNICAL FIELD

The present invention relates to a magnetic resonance imaging (MRI) apparatus and particularly, to a radio frequency (RF) coil for detecting a nuclear magnetic resonance signal.

BACKGROUND ART

An MRI apparatus is an apparatus for imaging an arbitrary cross-section across a subject using a nuclear magnetic resonance phenomenon. Specifically, the MRI apparatus is an apparatus for acquiring a sectional image by performing an image processing after irradiating atomic nuclei (usually hydrogen nuclei) in a subject placed in a spatially-uniform magnetic field (static magnetic field) with a radio frequency magnetic field, rotating macroscopic magnetization by atomic nuclei (magnetic resonance) with the direction of the static magnetic field as an axis, and detecting (receiving) a rotating magnetic field (circularly-polarized wave) generated in the process of returning to the original state while being rotated, as a nuclear magnetic resonance signal. In general, the direction of rotation of atomic nuclei is determined by the relationship between the static magnetic field direction and the nuclei.

Irradiation of a radio frequency magnetic field on a subject and detection of a nuclear magnetic resonance signal generated from the subject are performed by an RF coil having a loop part (coil loop) that performs an irradiation and detection. As the coil loop becomes smaller, a sensitivity region becomes narrower but the sensitivity becomes higher. In the meantime, as the coil loop becomes larger, the sensitivity region becomes wider but the sensitivity becomes lower. In this way, the RF coil has a trade-off relationship between the high sensitivity and the wide sensitivity region. Since this nuclear magnetic resonance signal is a very weak signal, high sensitivity is required for the RF coil.

There is a multi-channel array coil in which a plurality of RF coils is arranged in an array to achieve both high sensitivity and a wide range of sensitivity (see, e.g., Non-Patent Literature 1). Hereinafter, each RF coil in the multi-channel array coil is called a sub-coil.

In recent years, high-speed imaging using a difference in spatial sensitivity between sub-coils of the multi-channel array coil has become widespread (see, e.g., Non-Patent Literature 2). The high-speed imaging may be accelerated with the increased number of channels. Therefore, in recent years, the multi-channelization of multi-channel array coils has been further advanced to super multi-channel array coils of 32 channels and 128 channels which are now being distributed.

CITATION LIST

Non-Patent Literature

Non-Patent Literature 1: Roemer P B et al., "NMR Phased Array", Journal of Magnetic Resonance, USA, 1990, 16, p. 192-225
Non-Patent Literature 2: Klaas P P et al., "SENSE: Sensitivity Encoding for Fast MRI", Journal of Magnetic Resonance, USA, 1999, 42, p. 952-962

SUMMARY OF INVENTION

Technical Problem

Typically, when RF coils having the same resonance characteristics are arranged close to each other, they interfere with each other by a magnetic coupling. In the multi-channel array coil, when magnetic coupling occurs between the sub-coils, one of two magnetically-coupled sub-coils is affected by a current flowing through the other. As a result, in one sub-coil, signals are cancelled with each other, and the sensitivity may be decreased as much or the sensitivity of each sub-coil may differ from an expected one due to the generation of an unexpected rotating magnetic field. As a result, the image quality of an obtained reconfigured image is deteriorated.

The present invention has been made in view of the above circumstances and it is an object of the present invention to provide a multi-channel array coil used as an RF coil of an MRI apparatus, which is capable of suppressing cancellation of a current flowing through a sub-coil of a coupling counterpart, maintaining desired sensitivity and suppressing deterioration in image quality even when magnetic coupling occurs between sub-coils.

Solution to Problem

According to an aspect of the present invention, even when magnetic coupling occurs between the sub-coils constituting a multi-channel array coil used as an RF coil of an MRI apparatus, each of the sub-coils is connected to a signal processing circuit so that a phase difference between a rotating magnetic field generated by the sub-coil and a rotating magnetic field generated by the influence of a current flowing through a sub-coil of a coupling counterpart is less than 90 degrees in a region of interest.

Advantageous Effects of the Invention

According to the present invention, in a multi-channel array coil used as an RF coil of an MRI apparatus, even when magnetic coupling occurs between the respective sub-coils, it is possible to suppress cancellation of a current flowing through a sub-coil of a coupling counterpart to maintain the desired sensitivity and suppress deterioration of image quality.

BRIEF DESCRIPTION OF THE DRAWINGS

FIG. 5A is an explanatory view for explaining the configuration of an array coil used as the receiving RF coil of the first embodiment,
FIGS. 5B and 5C are explanatory views for explaining a transmission-reception magnetic coupling prevention circuit of the first embodiment.

DESCRIPTION OF EMBODIMENTS

First Embodiment

Figure 1A:
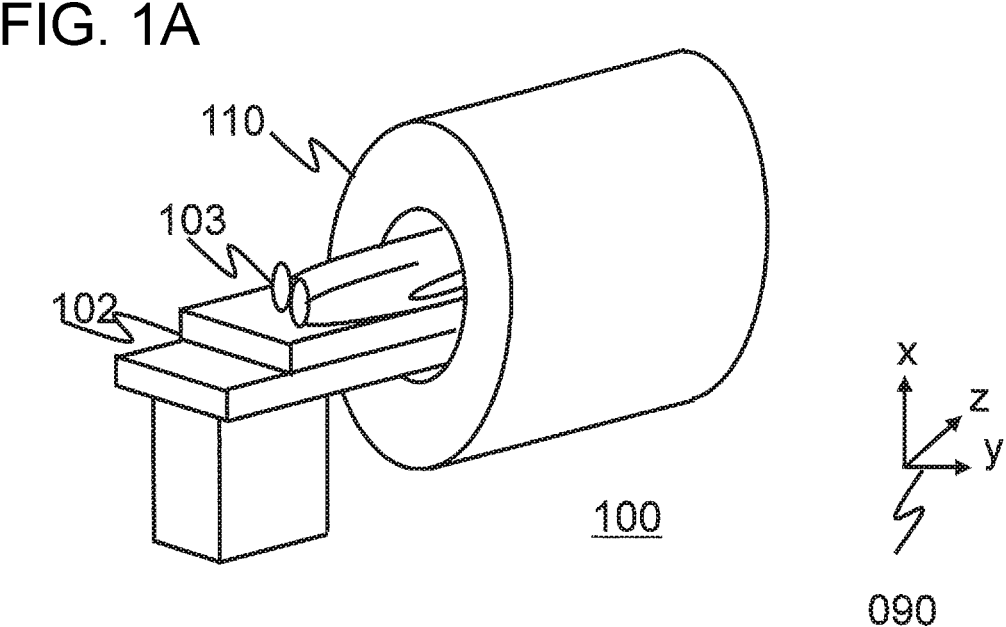
FIGS. 1A and 1B are schematic views of an MRI apparatus according to a first embodiment.

A first embodiment of the present invention will now be described. Hereinafter, throughout the drawings for explaining embodiments of the present invention, elements, parts or units having the same function are denoted by the same reference numerals unless otherwise specified, and explanation of which will not be repeated.

[Configuration of MRI Apparatus]

First, the overall configuration of an MRI apparatus of the first embodiment will be described with reference to FIGS. 1(a) and 1(b) which are schematic views of the MRI apparatus of the first embodiment.

Figure 1B:
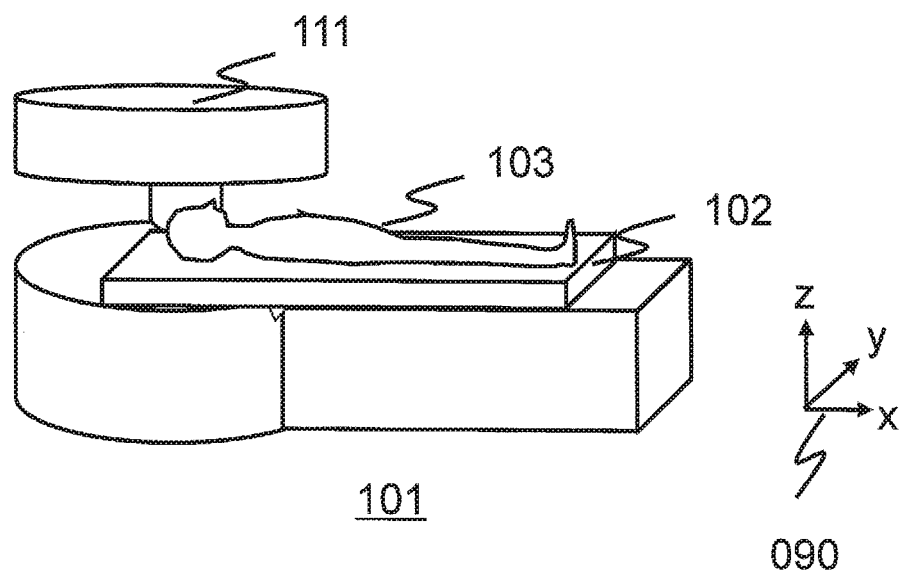

FIG. 1(a) illustrates a horizontal magnetic field type MRI apparatus 100 using a tunnel type magnet for generating a static magnetic field by a solenoid coil. The magnetic field direction coincides with the tunnel axial direction. FIG. 1(b) illustrates a hamburger-shaped (opened) vertical magnetic field type MRI apparatus 101 having two magnets vertically separated from each other in order to enhance the opening feeling. The magnetic field direction is the direction from one magnet to the other. The MRI apparatuses 100 and 101 include a table 102 on which an object to be inspected (subject) 103 is placed. The MRI apparatuses illustrated in these figures are illustrative only and are not particularly limited thereto.

In the first embodiment, in addition to the MRI apparatus 100 having a horizontal magnetic field type magnet 110 and the MRI apparatus 101 having a vertical magnetic field type magnet 111, various MRI apparatuses known in the art may be used, regardless of the form and type of apparatus. Hereinafter, in the first embodiment, the MRI apparatus 100 having the horizontal magnetic field type magnet 110 will be described by way of an example.

Throughout the following detailed description and the drawings, a coordinate system 090 is employed in which the static magnetic field direction corresponds to the z axis direction and the two directions perpendicular thereto correspond to the x axis direction and the y axis direction, respectively.

Figure 2:
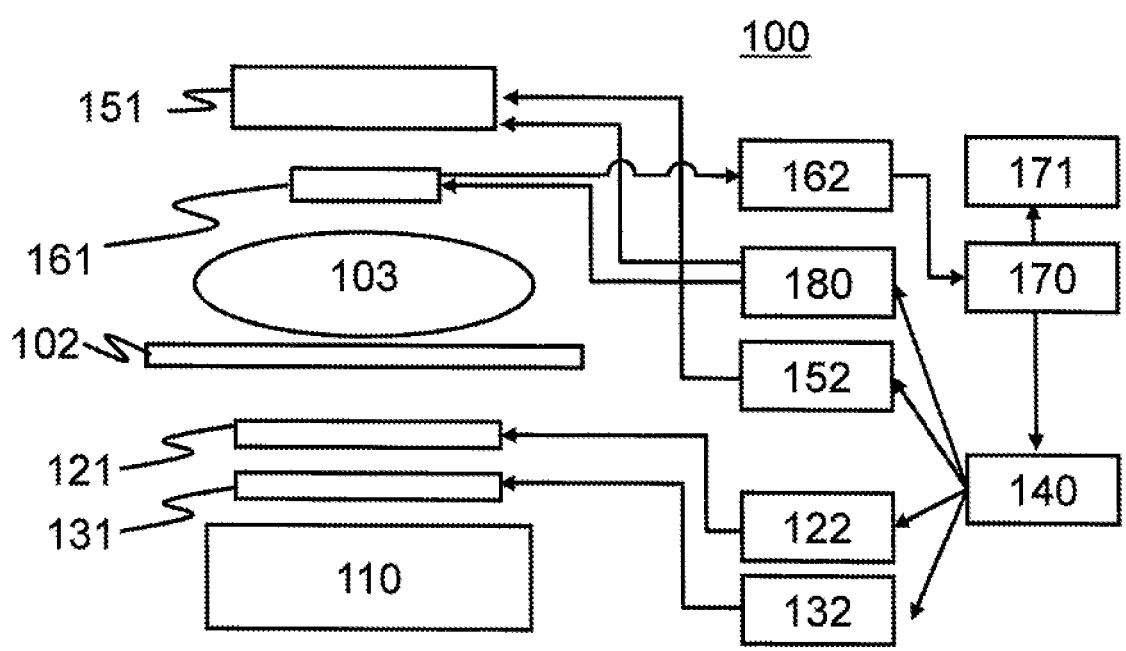
FIG. 2 is a block diagram of the MRI apparatus of the first embodiment.

FIG. 2 is a block diagram illustrating a schematic configuration of the MRI apparatus 100. Referring to the figure, the MRI apparatus 100 includes the horizontal magnetic field type magnet 110, a gradient magnetic field coil 131, a transmitting RF coil 151, a receiving RF coil 161, a gradient magnetic field power supply 132, a shim coil 121, a shim power supply 122, an RF magnetic field generator 152, a receiver 162, a magnetic coupling prevention circuit driver 180, a computer (PC) 170, a sequencer 140 and a display device 171. Reference numeral 102 denotes a table on which a subject 103 is placed.

The gradient magnetic field coil 131 is connected to the gradient magnetic field power supply 132 and generates a gradient magnetic field. The shim coil 121 is connected to the shim power supply 122 and adjusts the uniformity of the magnetic field. The transmitting RF coil 151 is connected to the RF magnetic field generator 152 and irradiates (transmits) an RF magnetic field to the subject 103 to generate a rotating magnetic field on the XY plane. The receiving RF coil 161 is connected to the receiver 162 and receives a nuclear magnetic resonance signal generated on the XY plane from the subject 103. The magnetic coupling prevention circuit driver 180 is connected to a magnetic coupling prevention circuit (which will be described later). The magnetic coupling prevention circuit is a circuit for preventing magnetic coupling between the transmitting RF coil 151 and the receiving RF coil 161, which is connected to the transmitting RF coil 151 and the receiving RF coil 161, respectively.

The sequencer 140 sends commands to the gradient magnetic field power supply 132, the RF magnetic field generator 152 and the magnetic coupling prevention circuit driver 180, respectively, to operate them. The commands are sent according to an instruction from the computer (PC) 170. In response to the instruction from the computer (PC) 170, a magnetic resonance frequency serving as the reference for detection in the receiver 162 is set. For example, according to a command from the sequencer 140, the subject 103 is irradiated with an RF magnetic field through the transmitting RF coil 151. A nuclear magnetic resonance signal generated from the subject 103 by irradiating the subject 103 with the RF magnetic field is detected by the receiving RF coil 161 and then detected by the receiver 162.

The computer (PC) 170 controls the overall operation of the MRI apparatus 100 and performs a variety of signal processing. For example, the computer (PC) 170 receives the signal detected by the receiver 162 via an A/D conversion circuit and performs a variety of signal processing such as image reconstruction and the like. The result of signal processing is displayed on the display device 171. Detected signals and measurement conditions are stored in a storage medium as necessary. In addition, the computer (PC) 170 sends commands to the sequencer 140 so as to operate the various devices at pre-programmed timing and intensity. Further, when it is necessary to adjust the uniformity of static magnetic field, the sequencer 140 sends a command to the shim power supply 122 to cause the shim coil 121 to adjust the static magnetic field uniformity.

[Configuration of Transmitting RF Coil and Receiving RF Coil]

Next, the transmitting RF coil 151 and the receiving RF coil 161 of the first embodiment will be described. In the first embodiment, as one example, an RF coil having a birdcage shape (birdcage-shaped RF coil) 300 is used as the transmitting RF coil 151 and an array coil 400 consisting of two looped RF coils (surface coils) arranged side by side is used as the receiving RF coil 161.

The resonance frequency of the birdcage-shaped RF coil 300 used as the transmitting RF coil 151 is adjusted to the resonance frequency of an element to be excited. In the first embodiment, it is adjusted to the magnetic resonance frequency of hydrogen nuclei capable of exciting hydrogen nuclei. The array coil 400 used as the receiving RF coil 161 is adjusted so as to detect a nuclear magnetic resonance signal of an element capable of being excited by birdcage-shaped RF coil 300.

A coil used as the transmitting RF coil 151 is not limited to the above-described birdcage-shaped RF coil 300. Any RF coil capable of generating an oscillating or rotating magnetic field on the XY plane and generating a magnetic resonance signal may be used.

[Arrangement and Connection Mode of Transmitting RF Coil and Receiving RF Coil]

Figure 3:
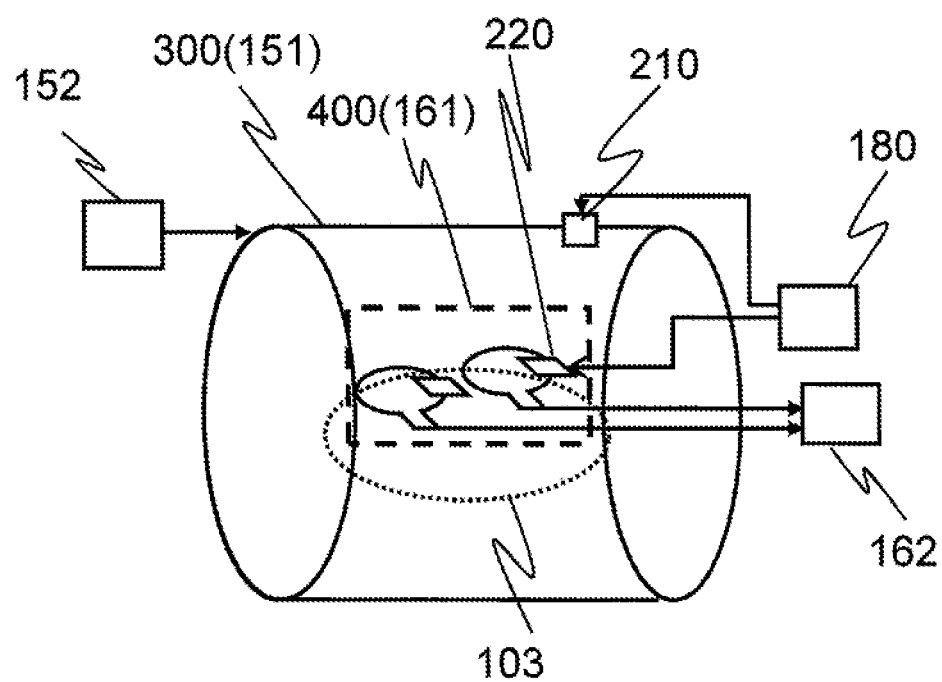
FIG. 3 is an explanatory view for explaining connection between a transmitting RF coil and a receiving RF coil of the first embodiment.
Figure 3:
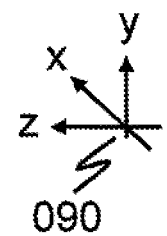

First, the arrangement of the birdcage-shaped RF coil 300 used as the transmitting RF coil 151 and the array coil 400 used as the receiving RF coil 161 and the connection mode of the birdcage-shaped RF coil 300, the array coil 400, the RF magnetic field generator 152, the receiver 162, and the magnetic coupling prevention circuit driver 180 will be described with reference to FIG. 3.

As illustrated in this figure, the birdcage-shaped RF coil 300 is arranged so that its axis coincides with the central axis of the magnet 110. The array coil 400 is disposed inside the birdcage-shaped RF coil 300. In addition, as described above, the birdcage-shaped RF coil 300 is connected to the RF magnetic field generator 152. Further, the array coil 400 is connected to the receiver 162.

Furthermore, in the first embodiment, the birdcage-shaped RF coil 300 includes a magnetic coupling prevention circuit 210 for preventing magnetic coupling with the array coil 400. This magnetic coupling prevention circuit 210 is a circuit for preventing magnetic coupling between the transmitting RF coil 151 (birdcage-shaped RF coil 300) and the receiving RF coil 161 (array coil 400), which is called a transmission-reception magnetic coupling prevention circuit 210. This transmission-reception magnetic coupling prevention circuit 210 is inserted in series with a straight line conductor (which will be described later) of the birdcage-shaped RF coil 300.

The array coil 400 includes a magnetic coupling prevention circuit 220 for preventing magnetic coupling with the birdcage-shaped RF coil 300. The magnetic coupling prevention circuit 220 is also a transmission-reception magnetic coupling prevention circuit for preventing magnetic coupling between the transmitting RF coil 151 (birdcage-shaped RF coil 300) and the receiving RF coil 161 (array coil 400). This transmission-reception magnetic coupling prevention circuit 220 is inserted in series with each surface coil constituting the array coil 400.

The magnetic coupling prevention circuit driver 180 is connected to the transmission-reception magnetic coupling prevention circuit 210 and the transmission-reception magnetic coupling prevention circuit 220.

[Birdcage-Shaped RF Coil]

Next, the birdcage-shaped RF coil 300 used as the transmitting RF coil 151 of the first embodiment will be described with reference to FIGS. 4(a) and 4(b). As described above, the birdcage-shaped RF coil 300 of the first embodiment is adjusted such that an element to be excited has its (magnetic) resonance frequency, and irradiates the XY plane with an RF magnetic field having the magnetic resonance frequency to produce a rotating magnetic field. Hereinafter, the magnetic resonance frequency of the RF magnetic field is called $f_0$.

Figure 4A:
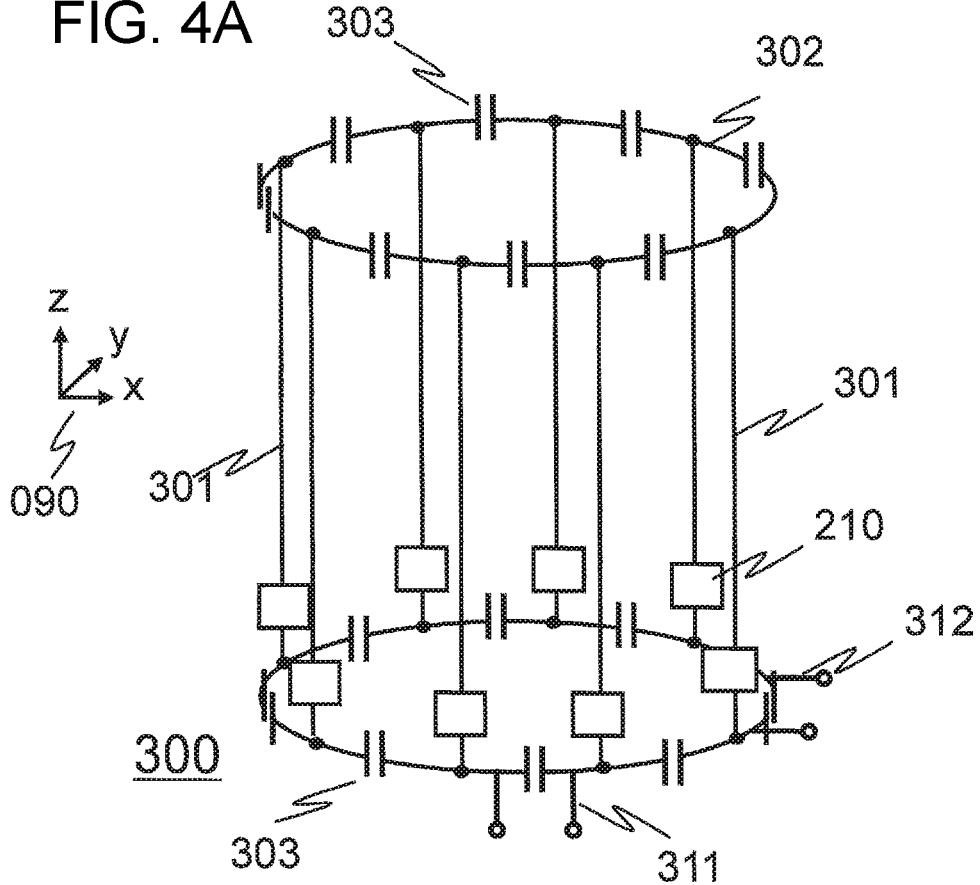
FIG. 4A is an explanatory view for explaining the configuration of a birdcage-shaped RF coil used as the transmitting RF coil of the first embodiment.

FIG. 4(a) is a block diagram for explaining the configuration of the birdcage-shaped RF coil 300 of the first embodiment. The birdcage-shaped RF coil 300 of the first embodiment includes a plurality of straight line conductors 301, an end conductor 302 connecting ends of the straight line conductors 301, and a capacitor 303 inserted in the end conductor 302. The aforementioned transmission-reception magnetic coupling prevention circuit 210 is inserted in series with each straight line conductor 301.

In addition, the birdcage-shaped RF coil 300 of the first embodiment has two input ports 311 and 312. The first input port 311 and the second input port 312 receive transmission signals whose phases are different by 90 degrees, respectively, and are configured such that an RF magnetic field is efficiently applied to the subject 103.

[Removal of Transmission-Reception Magnetic Coupling]

Figure 4B:
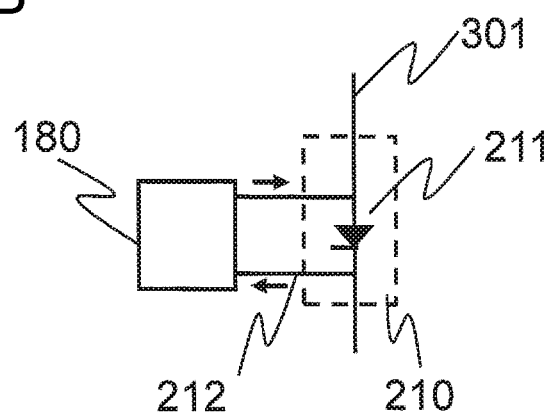
FIG. 4B is an explanatory view for explaining a transmission-reception magnetic coupling prevention circuit of the first embodiment.

FIG. 4(b) is a view for explaining the configuration of the transmission-reception magnetic coupling prevention circuit 210 inserted in the straight line conductor 301 of the birdcage-shaped RF coil 300 and the connection of the circuit 210 with the magnetic coupling prevention circuit driver 180.

The transmission-reception magnetic coupling prevention circuit 210 includes a PIN diode 211 and a control signal line 212. The PIN diode 211 is inserted in series with the straight line conductor 301 and the control signal line 212 is connected to both ends of the PIN diode 211. The control signal line 212 is connected to the magnetic coupling prevention circuit driver 180. A choke coil is inserted in the control signal line 212 in order to avoid mixing of high frequency.

The PIN diode 211 has a characteristic that it exhibits a high resistance (OFF) in a normal state and enters substantially in a conduction state (ON) when a value of a direct current flowing in the forward direction of the PIN diode 211 is equal to or larger than a predetermined value. In the first embodiment, this characteristic is used to control ON/OFF of the PIN diode 211 by a direct current output from the magnetic coupling prevention circuit driver 180. That is, at the time of transmitting an RF signal, a control current for making the PIN diode 211 conductive is flown so that the birdcage-shaped RF coil 300 functions as the transmitting RF coil 151. In addition, at the time of receiving a nuclear magnetic resonance signal, the control current is stopped and the birdcage-shaped RF coil 300 is brought into a high impedance state and set to the open state.

In this manner, in the first embodiment, by controlling the supply of the direct current (control current) from the magnetic coupling prevention circuit driver 180, the birdcage-shaped RF coil 300 functions as the transmitting RF coil 151 at the time of transmitting the RF signal, and the magnetic coupling with the array coil 400 functioning as the receiving RF coil 161 is removed in the open state at the time of receiving the nuclear magnetic resonance signal.

[Array Coil]

Next, the array coil 400 used as the receiving RF coil 161 of the first embodiment will be described with reference to FIGS. 5(a) to 8(c). As described above, the array coil 400 of the first embodiment includes two sub-coils 410. Each of the two sub-coils 410 is capable of receiving a nuclear magnetic resonance signal and functions as a channel.

FIG. 5(a) is a block diagram for explaining the configuration of the array coil 400 of the first embodiment. The two sub-coils 410 constituting the array coil 400 of the first embodiment are referred to as a first sub-coil 410A and a second sub-coil 410B, respectively. The first sub-coil 410A and the second sub-coil 410B are surface coils each having a loop formed on a plane. In addition, the first sub-coil 410A and the second sub-coil 410B each receive a nuclear magnetic resonance signal which is then sent to the receiver 162.

Hereinafter, when it is not necessary to distinguish the constituent elements of the sub-coil 410 constituting the array coil 400, particularly for each sub-coil 410, the last letter of the reference numeral is omitted.

The first sub-coil 410A includes a loop coil part 420 (first loop coil part 420A) for receiving a nuclear magnetic resonance signal (RF signal), a low (input) impedance signal processing circuit 430 (first low input impedance signal processing circuit 430A) for receiving a RF signal detected by the loop coil part 420A, and a magnetic coupling adjusting part 441 (first magnetic coupling adjusting part 441A) for connecting the loop coil part 420 and the low input impedance signal processing circuit 430. The magnetic coupling adjusting part 441 is composed of at least one of a capacitor and an inductor.

The loop portion (first loop 421A) of the first loop coil part 420A is formed of a conductor. The first loop coil part 420A includes a capacitor 424A inserted in parallel with the inductor component of the first loop 421A. This inductor component and the capacitor 424A constitute a parallel resonance circuit. This capacitor 424A is referred to as a first parallel capacitor 424A to distinguish it from other capacitors.

In addition, a capacitor 422A for adjusting the resonance frequency and the magnetic coupling prevention circuit 220 are inserted in series in the first loop 421A. This capacitor 422A is referred to as a first series capacitor 422A to distinguish it from other capacitors. Although the case where two first series capacitors 422A are provided is exemplified here, the number of the first series capacitors 422A may be one or three or more.

In this manner, the first sub-coil 410A of the first embodiment includes, as circuit elements for adjustment, the first magnetic coupling adjusting part 441A, the first series capacitor 422A inserted in series with the inductor component of the first loop 421A, and the first parallel capacitor 424A inserted in series with the inductor component to make the first loop coil part 420A a parallel resonance circuit.

The low input impedance signal processing circuit 430A has two terminals on the side of the loop coil part 420A (input side) and two terminals on the opposite side (output side). One terminal of the loop coil part 420A side (input side) is connected to one end of the parallel capacitor 424A of the loop coil part 420A via the magnetic coupling adjusting part 441A. The other terminal on the input side is directly connected to the other end of the parallel capacitor 424A of the loop coil part 420A. One terminal on the opposite side (output side) to the loop coil part 420A of the low input impedance signal processing circuit 430A is connected to the receiver 162 via a coaxial cable. The other terminal on the output side is connected (grounded) to a ground 490 via a coaxial cable.

The transmission-reception magnetic coupling prevention circuit 220 removes the magnetic coupling with the birdcage-shaped RF coil 300 serving as the transmitting RF coil 151.

The second sub-coil 410B has the same configuration as the first sub-coil 410A. That is, the second sub-coil 410B includes a second loop coil part 420B, which is a parallel resonance circuit, a second low input impedance signal processing circuit 430B, and a second magnetic coupling adjusting part 441B connecting the second loop coil part 420B and the second low input impedance signal processing circuit 430B. The second loop coil part 420B includes a loop (second loop 421B) formed of a conductor, a second series capacitor 422B inserted in series with the inductor component of the second loop 421B, and a second parallel capacitor 424B inserted in series with the inductor component to make the second loop coil part 420B a parallel resonance circuit.

In the second sub-coil 410B, two terminals on the loop coil part 420B side (input side) of the low input impedance signal processing circuit 430B are connected to both ends of the parallel capacitor 424B respectively, but only one of the terminals being connected via the magnetic coupling adjusting part 441B. One of two terminals on the opposite side (output side) is connected to the receiver 162 via a coaxial cable and the other is connected (grounded) to the ground 490 via a coaxial cable.

Removal of the magnetic coupling between the transmitting RF coil 151 (birdcage-shaped RF coil 300) and the receiving RF coil 161 (array coil 400) by the transmission-reception magnetic coupling prevention circuit 220 will be described below. FIG. 5(b) is a view for explaining the configuration of the transmission-reception magnetic coupling prevention circuit 220 inserted in a loop 421 and the connection between the transmission-reception magnetic coupling prevention circuit 220 and the magnetic coupling prevention circuit driver 180.

The transmission-reception magnetic coupling prevention circuit 220 includes a PIN diode 221, an inductor 222, and a control signal line 223.

The PIN diode 221 and the inductor 222 are connected in series and are connected in parallel to a capacitor 423. Here, the capacitor 423 is a capacitor inserted in the loop 421. The control signal line 223 is connected to both ends of the PIN diode 221. The control signal line 223 is connected to the magnetic coupling prevention circuit driver 180. A choke coil (not illustrated) is inserted in the control signal line 223 in order to avoid mixing of high frequencies. The inductor 222 and the capacitor 423 are adjusted so as to resonate in parallel at the frequency of the nuclear magnetic resonance signal to be received.

A parallel resonance circuit generally has a characteristic of high impedance (high resistance) at a resonance frequency. Therefore, when a current flows through the PIN diode 221, the PIN diode 221 is turned ON, and the capacitor 423 of the loop 421 resonates in parallel with the inductor 222 at the frequency of the received nuclear magnetic resonance signal to become a high impedance state. Accordingly, with the frequency of the received nuclear magnetic resonance signal, a portion of the loop coil part 420 becomes a high impedance state to be in an open state, and the sub-coil 410 having the loop coil part 420 is also in an open state.

In this manner, when the PIN diode 221 is turned ON by a current flowing therethrough, the magnetic coupling between the sub-coils 410A and 410B and the birdcage-shaped RF coil 300 is removed. Accordingly, the magnetic coupling between the array coil 400 having each sub-coil 410 as a coil element and the birdcage-shaped RF coil 300 is removed.

The number of transmission-reception magnetic coupling prevention circuits 220 inserted in the sub-coil 410 is not limited thereto. Two or more transmission-reception magnetic coupling prevention circuits 220 may be inserted in each loop 421. By inserting a plurality of transmission-reception magnetic coupling prevention circuits 220, the magnetic coupling between the array coil 400 and the birdcage-shaped RF coil 300 may be sufficiently lowered.

The configuration of the transmission-reception magnetic coupling prevention circuit 220 is not limited to the above-described configuration. For example, a cross diode 221m may be used in place of the PIN diode 221, as in a modification of a transmission-reception magnetic coupling prevention circuit 220m illustrated in FIG. 5(c). Accordingly, when a large signal flows through a conductor constituting the loop 421, the cross diode 221m is turned ON, and the capacitor 423 of the loop 421 resonates in parallel resonance with the inductor 222 at the frequency of the received nuclear magnetic resonance signal to become a high impedance state. In this case, the magnetic coupling prevention circuit driver 180 may be excluded.

[Arrangement and Adjustment of Each Sub-Coil]

In the array coil 400 of the first embodiment, each of the first sub-coil 410A and the second sub-coil 410B is adjusted so as to be able to receive a nuclear magnetic resonance signal. The first sub-coil 410A is adjusted so that the resonance frequency of the first sub-coil 410A alone is different from the nuclear magnetic resonance frequency that is the frequency of a nuclear magnetic resonance signal to be transmitted/received. In addition, the first sub-coil 410A is arranged at a position or configuration capable of magnetically coupling with the second sub-coil 410B and is adjusted such that the first loop 421A and the second loop 421B form a circulating current path respectively and resonate at the nuclear magnetic resonance frequency by intentionally magnetic coupling with the second sub-coil 410B. Specifically, the first sub-coil 410A is arranged and adjusted at a position at which the resonance frequency characteristic of the sub-coil 410A alone is varied depending on the presence or absence of the second sub-coil 410B.

[Arrangement]

In addition, the loop coil part 420A of the first sub-coil 410A and the loop coil part 420B of the second sub-coil 410B are arranged at positions at which a rotating magnetic field (nuclear magnetic resonance signal) generated in a space between the first sub-coil 410A and the second sub-coil 410B is detectable as an RF signal.

At this time, in the array coil 400, the first sub-coil 410A and the second sub-coil 410B are arranged at positions at which magnetic coupling can be made. That is, the loop coil part 420A of the first sub-coil 410A and the loop coil part 420B of the second sub-coil 410B are arranged on substantially the same plane at positions at which magnetic fields produced by the first sub-coil 410A and the second sub-coil 410B are able to interfere with each other. Portions of the coil elements may be overlapped as long as the magnetic coupling between the first sub-coil 410A and the second sub-coil 410B occurs.

Figure 6A:
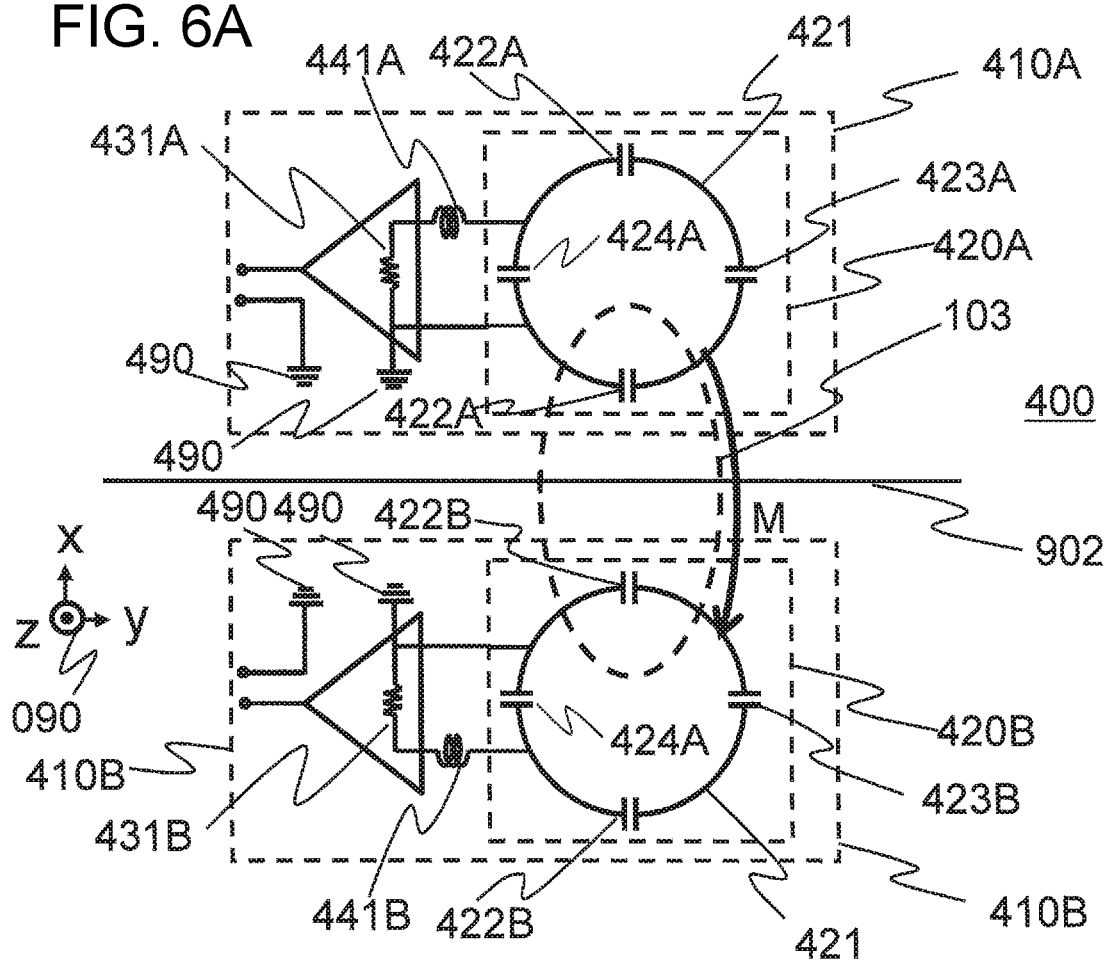
FIGS. 6A and 6B are explanatory views for explaining the arrangement of an array coil of the first embodiment.
Figure 6B:
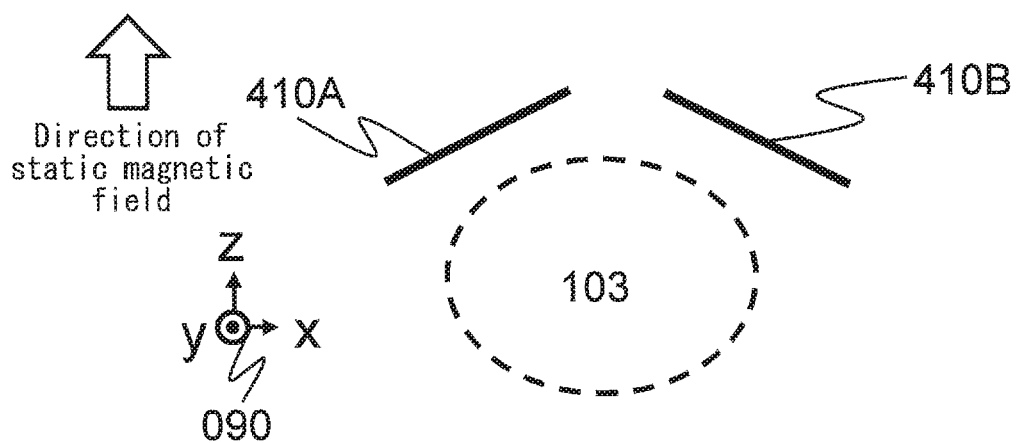

A specific example of such an arrangement will be described with reference to FIGS. 6(a) and 6(b). FIGS. 6(a) and 6(b) are views for explaining the arrangement of the first sub-coil 410A and the second sub-coil 410B constituting the array coil 400 used as the receiving RF coil 161 of the first embodiment.

In FIG. 6(a), as illustrated in a coordinate system 090, the vertical direction of the paper surface is the x-axis direction, the horizontal direction thereof is the y-axis direction, and the direction perpendicular to the paper surface is the z-axis direction. In FIG. 6(b), as illustrated in the coordinate system 090, the vertical direction of the paper surface is the z-axis direction, the horizontal direction thereof is the x-axis direction, and the direction perpendicular to the paper surface is the y-axis direction.

As illustrated in FIGS. 6(a) and 6(b), in the first embodiment, the first sub-coil 410A and the second sub-coil 410B are arranged in such a manner that the planes formed by the loops 421 of the respective loop coil parts 420 are relatively close to the plane perpendicular to the static magnetic field direction (z-axis direction). Further, the loops 421 of the loop coil parts 420 are circular. Further, as illustrated in FIG. 6(a), the first sub-coil 410A and the second sub-coil 410B are arranged in line symmetry with a line 902 drawn between both in the figure.

For example, the diameter of each of the loop 421A of the first loop coil part 420A and the loop 421B of the second loop coil part 420B is 100 mm. In this case, as a distance and position where magnetic coupling occurs, the first sub-coil 410A is arranged on a plane rotated counterclockwise by 20 degrees from the xy plane with the y-axis as a rotation axis, and the second sub-coil 410B is arranged on a plane rotated clockwise by 20 degrees from the xy plane with the y-axis as the rotation axis. The distance between the origins of the circles of the circular loops 421 of the two sub-coils 410 is set to 132 mm.

When the two sub-coils 410A are arranged in a positional relationship where magnetic coupling occurs, the magnitude M of the mutual inductance is expressed by the following equation (1).

[Equation 1]

$$M = k\sqrt{L_{11}L_{21}} \qquad (1)$$

Wherein, k is a magnetic coupling coefficient, which is a value indicating a ratio of a magnetic flux coupled between the magnetic flux created by the first sub-coil 410A and the second sub-coil 410B. The magnetic coupling coefficient k takes a value from 0 to 1. $L_{11}$ is the magnitude of the inductor component of the loop 421A of the first sub-coil 410A. $L_{21}$ is the magnitude of the inductor component of the loop 421B of the second sub-coil 410B.

As illustrated in FIG. 6(a), low input impedance signal amplifiers 431A and 431B are used as the first low input impedance signal processing circuit 430A and the second low input impedance signal processing circuit 430B, respectively.

When the low input impedance signal amplifiers 431 are used as the low input impedance signal processing circuit 430, it is possible to immediately amplify a signal detected by the loop coil part 420, so that data with little noise may be acquired. The input impedance of the low input impedance signal amplifier 431 is 2Ω. It should be noted that the low input impedance signal processing circuit 430 is not limited to the signal amplifier 431 having low input impedance.

[Adjustment of Circuit Element]

Next, adjustment of each circuit element of the array coil 400 will be described. The following description will be focused on an operation at the time of reception. In the first embodiment, the magnetic coupling between the transmitting RF coil 151 and the receiving RF coil 161 is removed by the above-described method using the transmission-reception magnetic coupling prevention circuits 210 and 220. Here, the transmitting RF coil 151 is always in an open state, and the explanation of the removal of the magnetic coupling between the transmitting RF coil 151 and the receiving RF coil 161 is omitted.

The first sub-coil 410A and the second sub-coil 410B of the array coil 400 of the first embodiment realize the above-described functions by adjusting values of the first magnetic coupling adjusting part 441A, the second magnetic coupling adjusting part 441B, the first series capacitors 422A and 423A, the second series capacitors 422B and 423B, the first parallel capacitor 424A and the second parallel capacitor 424B.

[Principle of Parallel Resonance Circuit Characteristics]

Prior to description on the adjustment of each circuit element, the operation of the general parallel resonance circuit will be described with reference to FIGS. 7(a) and 7(b) which are views for explaining the operation of a parallel resonance circuit.

Figure 7A:
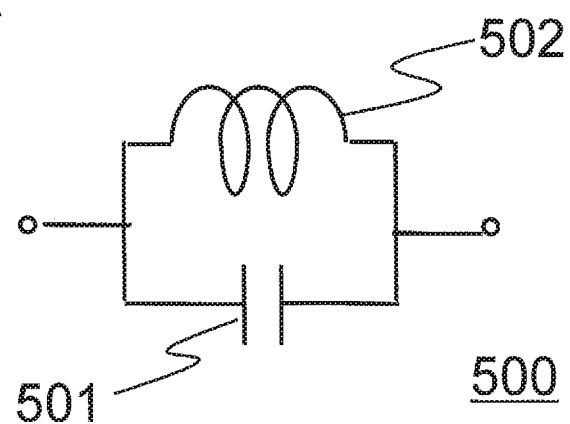
FIGS. 7A and 7B are explanatory views for explaining the operation of a general parallel resonance circuit.

As illustrated in FIG. 7(a), a parallel resonance circuit 500 includes an inductor 502(L) and a capacitor 501(C) connected in parallel. Assuming that the frequency of a voltage applied to the parallel resonance circuit 500 is f and the angular frequency thereof is ω (ω=2πf), an impedance Z at both ends of the parallel resonance circuit 500 is expressed by the following equation (2).

[Equation 2]

$$\frac{1}{Z} = j\omega C + \frac{1}{j\omega L} \quad (2)$$

Figure 7B:
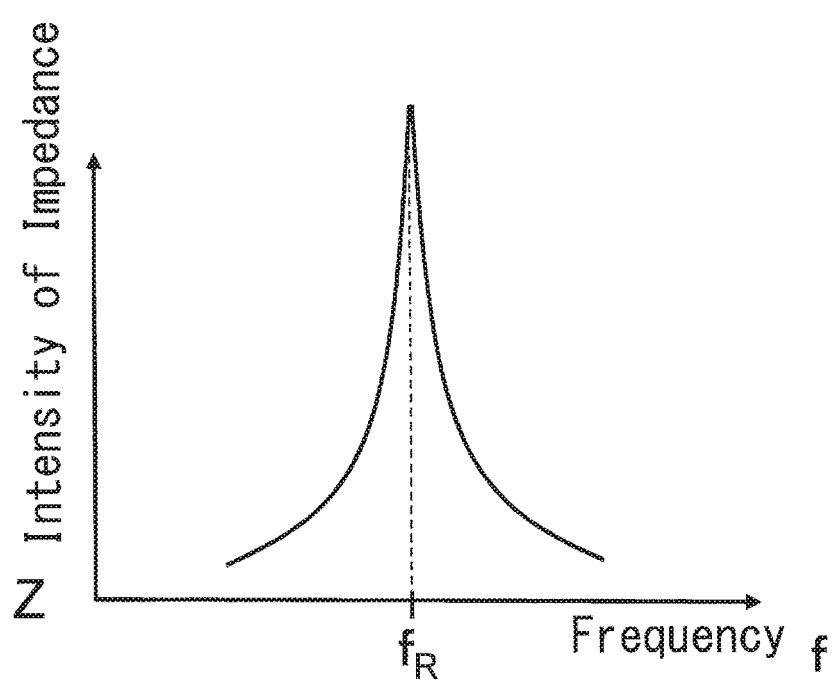

The impedance Z is varied depending on an applied frequency f, as illustrated in FIG. 7(b), and resonates at a frequency f=$f_R$. That is, the impedance Z at both ends of the parallel resonance circuit 500 becomes maximal at the frequency $f_R$.

At each frequency (f<$f_R$) lower than the resonant frequency $f_R$ of the parallel resonance circuit 500, the impedance Z is expressed by the following equation (3) and the parallel resonance circuit 500 operates as an inductive reactance (inductor).

[Equation 3]

$$Z = \frac{1 - (f/f_R)^2}{j2\pi fL} \quad (3)$$

Wherein, an apparent inductance value L' of the parallel resonance circuit 500 is expressed by the following equation (4).

[Equation 4]

$$L' = \frac{L}{1 - (f/f_R)^2} \quad (4)$$

In the meantime, at each frequency (f>$f_R$) higher than the resonant frequency $f_R$ of the parallel resonance circuit 500, the impedance Z is expressed by the following equation (5) and the parallel resonance circuit 500 operates as a capacitive reactance (capacitor).

[Equation 5]

$$Z = j2\pi fC \frac{(f/f_R)^2 - 1}{(f/f_R)^2} \quad (5)$$

Wherein, an apparent capacitance value C' of the parallel resonance circuit 500 is expressed by the following equation (6).

[Equation 6]

$$C' = \frac{(f/f_R)^2 - 1}{(f/f_R)^2} C \quad (6)$$

In this manner, the parallel resonance circuit 500 operates differently with its resonance frequency $f_R$ as a boundary depending on the frequency f of the applied voltage. In the first embodiment, each circuit element of the array coil 400 is adjusted using this property of the parallel resonance circuit 500.

Hereinafter, the adjustment of each circuit element of the array coil 400 of the first embodiment will be described using an equivalence circuit of the array coil 400.

Figure 8A:
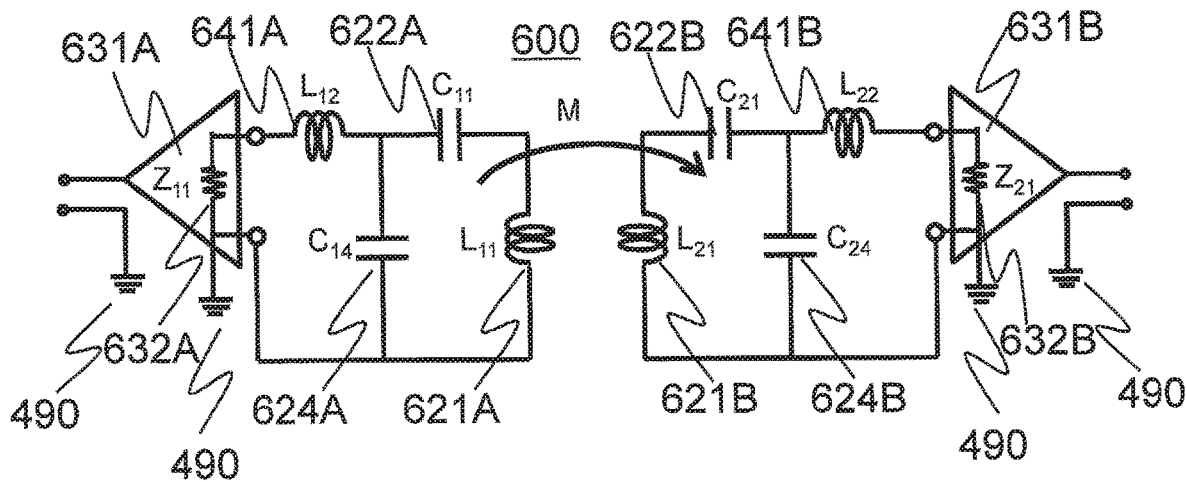
FIGS. 8A to 8C are explanatory views for explaining the operation of the array coil of the first embodiment.

FIG. 8(a) illustrates an equivalent circuit 600 of the array coil 400 of the first embodiment. In this figure, a value $L_{11}$ of an inductor 621A is the inductor component of the first loop 421A and a value $C_{11}$ of a series capacitor 622A is a combined value of the series capacitors 422A and 423A inserted in the first loop 421A. Similarly, a value $L_{21}$ of an inductor 621B is the inductor component of the second loop 421A and a value $C_{21}$ of a series capacitor 622B is a combined value of the series capacitors 422B and 423B inserted in the second loop 421B.

In addition, a value $C_{14}$ of a parallel capacitor 624A is a value of the parallel capacitor 424A and a value $C_{24}$ of a parallel capacitor 624B is a value of the parallel capacitor 424B.

An inductor is used for the magnetic coupling adjusting part 441. The value $L_{12}$ of the inductor 641A is the value of an inductor of the first magnetic coupling adjusting part 441A. The value $L_{22}$ of the inductor 641B is the value of an inductor of the second magnetic coupling adjusting part 441B. In the first embodiment, an inductor is used for the magnetic coupling adjustment part 441, but the present invention is not limited thereto. Typically, the parallel capacitor 624 and the magnetic coupling adjusting part 441 are connected by a conductor. Since this conductor also has an inductor component, a parallel resonance circuit is formed by the parallel capacitor 624, the magnetic coupling adjusting part 441 and the inductor component of the conductor connecting them, without adding a further inductor. If the resonance frequency of this parallel resonance circuit can be adjusted by any method, the magnetic coupling adjusting part 441 may be a capacitor. Alternatively, a parallel circuit of a capacitor and an inductor may be used. In the following description, for simplification of description, it is assumed that there is no inductor component of the conductor connecting the parallel capacitor 624 and the magnetic coupling adjusting part 441.

A value $Z_{11}$ of an impedance 632A is a value of the input impedance of the low input impedance signal amplifier 431A used as the first low input impedance signal processing circuit 430A. A value $Z_{21}$ of an impedance 632B is a value of the input impedance of the low input impedance signal amplifier 431B used as the second low input impedance signal processing circuit 430B. Since these impedances $Z_{11}$ and $Z_{21}$ are sufficiently low, they are hereinafter considered as 0Ω (short circuit).

A mutual inductance M is a mutual inductance value of the first loop coil part 420A (620A) and the second loop coil part 420B (620B).

Here, it is assumed that the frequency (nuclear magnetic resonance frequency) of a nuclear magnetic resonance signal to be detected is $f_0$, the resonance frequency of the first sub-coil 410A (610A) alone is $f_{10}$, the resonance frequency of the second sub-coil 410B (610B) alone is $f_{20}$, the resonance frequency of the first loop coil part 420A (620A) which is a parallel resonance circuit is $f_{12}$, and the resonance frequency of the second loop coil part 420B (620B) is $f_{22}$.

Further, when arranged as illustrated in FIGS. 6(a) and 6(b), it is assumed that the resonance frequency of the first sub-coil 410A (610A) (hereinafter referred to as a first resonance part) excluding the first low input impedance signal processing circuit 430A (631A) is $f_{11}$ when looked at from the first low input impedance signal processing circuit 430A (631A) at the time of signal reception. In addition, it is assumed that the resonance frequency of the second sub-coil 410B (610B) (hereinafter referred to as a second resonance part) excluding the first low input impedance signal processing circuit 430A (631A) is $f_{21}$ when looked at from the second low input impedance signal processing circuit 430B (631A) at the time of signal reception.

Each circuit element of the array coil 400 of the first embodiment is adjusted so as to satisfy the following equations (7) to (10).

$$f_{11} = f_{22} = f_{20} = f_0 \quad (7)$$

$$f_{10} \neq f_0 \quad (8)$$

[Equation 9]

$$\frac{1}{2\pi\sqrt{L_{22}C_{24}}} \neq f_0 \quad (9)$$

$$\frac{1}{2\pi\sqrt{L_{12}C_{14}}} \neq f_0 \quad (10)$$

By adjusting each circuit element according to the equation (9), the resonance frequency of a parallel resonance circuit (hereinafter referred to as an $L_{22}C_{24}$ resonance circuit) of the adjustment inductor 441B (641B) of the second sub-coil 410B (610B) and the parallel capacitor 424B (624B) differs from the nuclear magnetic resonance frequency $f_0$. Therefore, at the time of signal reception, both ends of the capacitor 424B of the second sub-coil 410B do not have high resistance but are magnetically coupled to the first sub-coil 410A.

Figure 8B:
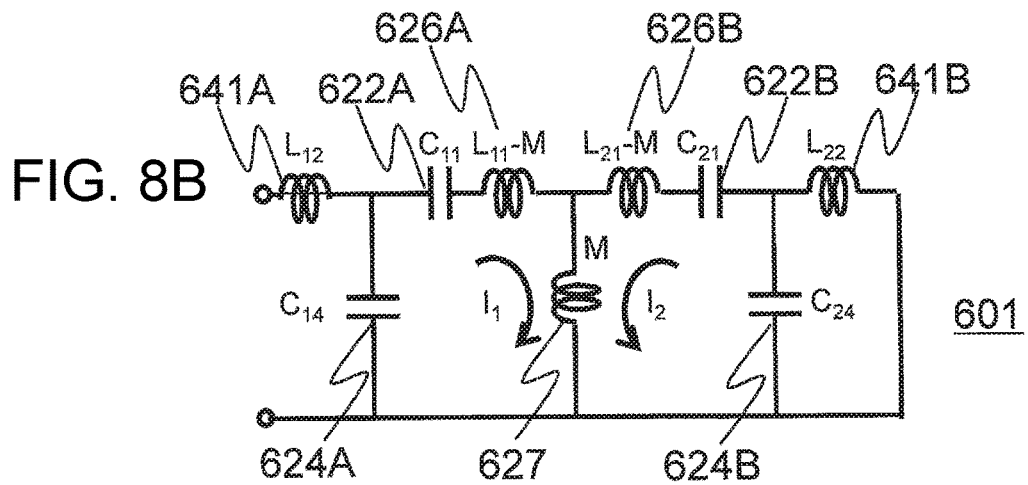

FIG. 8(b) illustrates an equivalent circuit 601 of the first sub-coil 410A (first resonance part) excluding the first low input impedance signal processing circuit 430A (631A) after adjustment. The equivalent circuit illustrated in FIG. 8(b) is an equivalent circuit of the first resonance part in a state where the first loop coil part 420A and the second loop coil part 420B are magnetically coupled by the above adjustment, when looked at from the first low input impedance signal processing circuit 430A (631A).

That is, at the time of signal reception, as illustrated in FIG. 8(b), the first resonance part of the first sub-coil 410A becomes a circuit 601 in which the inductor component $L_{11}$ of the first loop 421A and the inductor component $L_{21}$ of the second loop 421B are magnetically coupled to each other.

In the figure, an inductor 627 has the mutual inductance M, the value $L_{11}$-M of an inductor 626A and the value $L_{21}$-M of an inductor 626B obtained by removing the mutual inductance M from the inductor component of the loop 421.

In addition, by adjusting each circuit element according to the equation (10), the resonance frequency of a parallel resonance circuit (hereinafter referred to as an $L_{12}C_{14}$ resonance circuit) of the adjustment inductor 441A (641A) of the first sub-coil 410A (610A) and the parallel capacitor 424A (624A) becomes equal to the nuclear magnetic resonance frequency $f_0$. Accordingly, at the time of signal reception, both ends of the capacitor 424A of the first sub-coil 410A have high resistance. Therefore, the second sub-coil 410B is not magnetically coupled to the first sub-coil 410A.

Figure 8C:
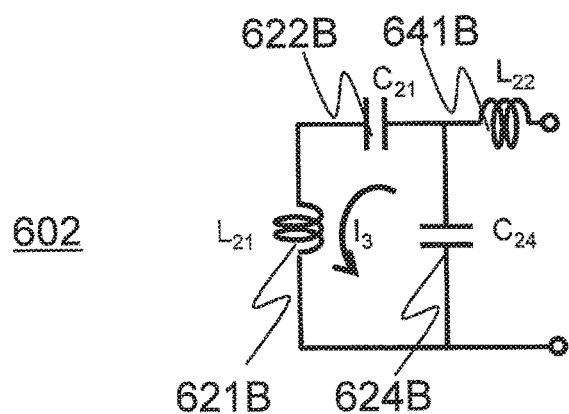

FIG. 8(c) illustrates an equivalent circuit 602 of the second sub-coil 410B (second resonance part) excluding the low input impedance signal processing circuit 430B (631B) when adjusted according to the equation (10), when looked at from the second low input impedance signal processing circuit 430B (631B).

The first sub-coil 410A is adjusted to prevent magnetic coupling with the first sub-coil 410B at the time of signal reception. Therefore, at the time of signal reception, the resonance part of the second sub-coil 410B becomes the same circuit 602 as in the case of the second sub-coil 410B alone, as illustrated in FIG. 8(c).

In addition, by adjusting each circuit element according to the equation (8), the resonance frequency $f_{10}$ of the first sub-coil 410A alone differs from the nuclear magnetic resonance frequency $f_0$.

In addition, by adjusting each circuit element according to the equation (7), the resonance frequency $f_{20}$ of the second sub-coil 410B alone, the resonance frequency $f_{11}$ of the first resonance part at the time of signal reception, and the resonance frequency $f_{22}$ of the second loop coil part 420B become equal to the nuclear magnetic resonance frequency $f_0$. Thus, the second sub-coil 410B can detect a nuclear magnetic resonance signal by itself.

In addition, as described above, the first sub-coil 410A is magnetically coupled to the second sub-coil 410B at the time of signal reception. At this time, the resonance frequency of the first resonance part becomes equal to the nuclear magnetic resonance frequency $f_0$. Therefore, the sub-coil 410A may also detect the nuclear magnetic resonance signal in a state of being magnetically coupled.

In addition, as described above, the adjustment is made based on the values of the series capacitor 622, the parallel capacitor 624 and the adjustment inductor 641. Further, in the first embodiment, the value of the inductor 621 of the loop 421 cannot be changed since it is determined by the shape of the loop 421. Further, the mutual inductance value M is determined by the shape and arrangement relationship.

[Phase Adjustment at the Time of Signal Reception]

Further, in the array coil 400 of the first embodiment, the loop coil part 420 and the low impedance signal processing circuit 430 are connected such that a phase difference between a rotating magnetic field generated in a region of interest of the subject by the second loop coil part 420B alone and a rotating magnetic field generated in the region of interest of the subject by magnetic coupling of the first loop coil part 420A with the second loop coil part 420B is less than 90 degrees.

As described above, in the array coil 400 of the first embodiment, the second loop 421B functions as two circuits at the time of signal reception, that is, the circuit 601 by magnetic coupling and the circuit 602 alone. Accordingly, a current flowing through the virtual circuit 601 at the time of magnetic coupling and a current flowing through the circuit 602 alone flow through the second loop 421B. That is, two current modes of a first current mode formed in the circuit 601 and a second current mode formed in the circuit 602 are simultaneously formed.

[Determination of Ground Terminal]

A method of determining the connection between the loop coil part 420 and the low input impedance signal processing circuit 430 of the first embodiment will be described by way of a specific example. Here, a case where current is supplied to the circuit will be described by way of an example, by applying the reciprocity theorem to a current flows through the coil side terminal of the low input signal processing circuit at the time of signal reception, that is, a detected signal.

In addition, on the basis of the connection between the first loop 421A in the first sub-coil 410A and the first low input impedance signal processing circuit 430A, the above-described connection adjustment is performed in the second loop 421B in the second sub-coil 410B and the second low input impedance signal processing circuit 430B.

Figure 9A:
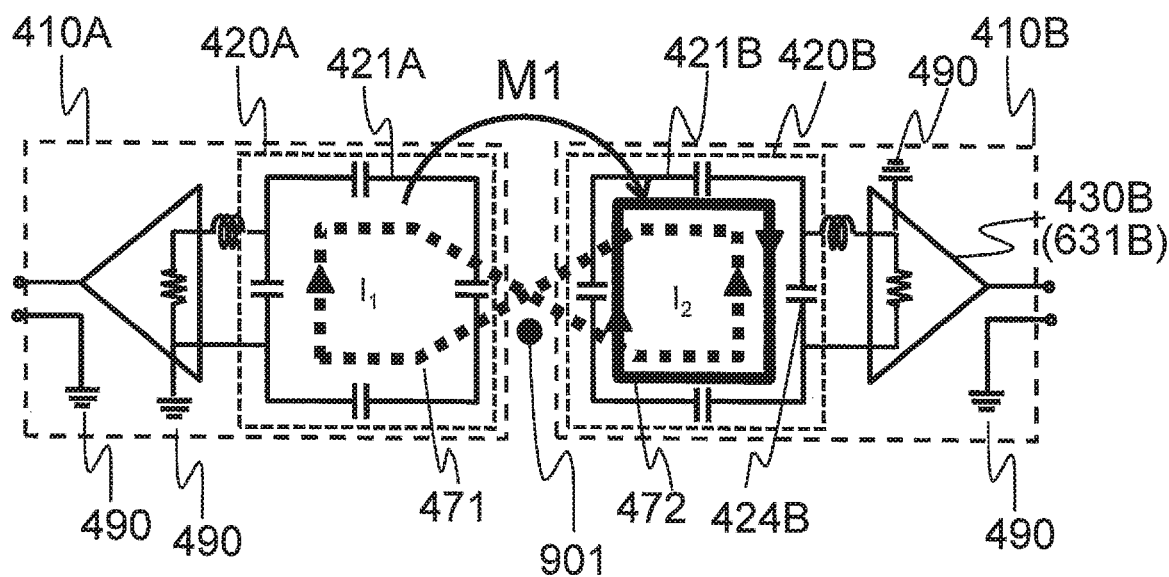
FIGS. 9A and 9B are explanatory views for explaining the direction of a current flowing through the array coil of the first embodiment.
Figure 9B:
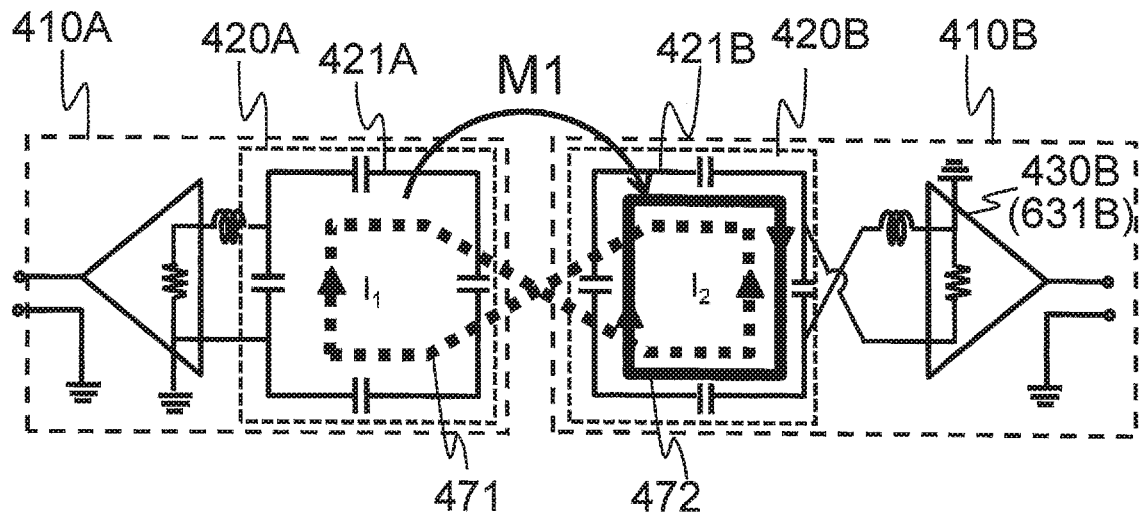
Figure 10A:
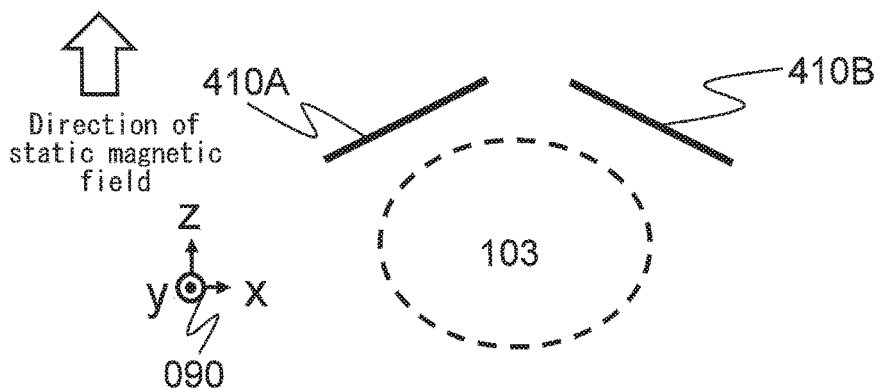
FIGS. 10A to 10C are explanatory views for explaining the phase of a signal generated at an input terminal of a low input impedance signal processing circuit of the first embodiment.
Figure 10B:
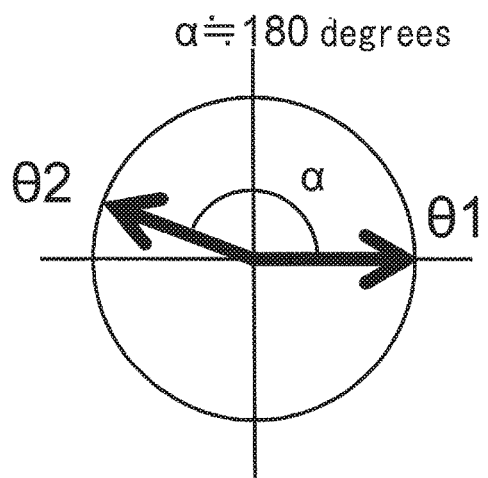
Figure 10C:
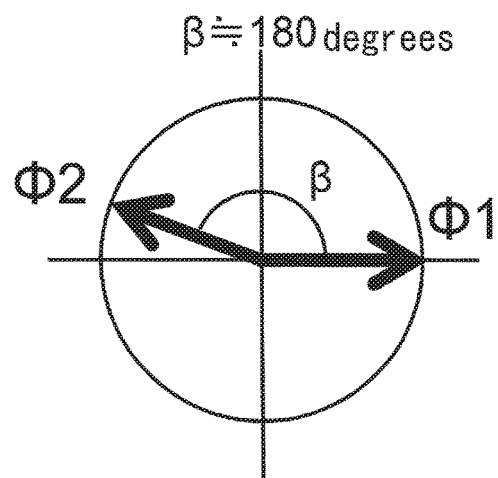
Figure 10D:
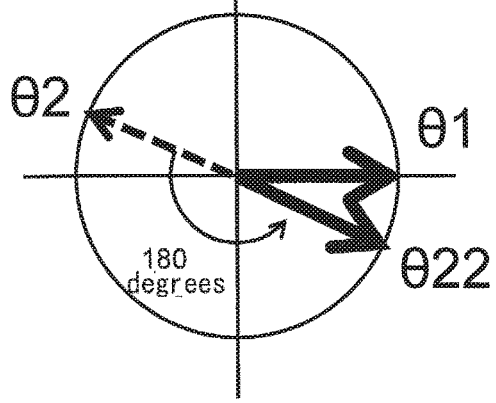
Figure 10E:
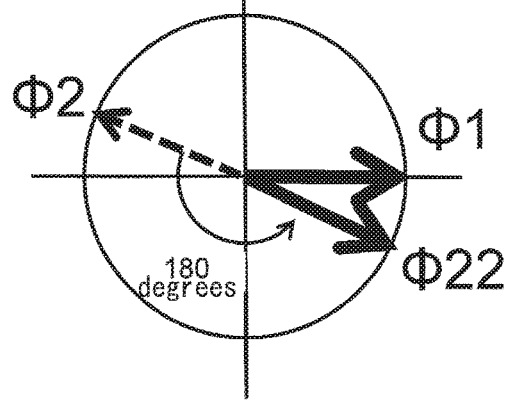

First, as illustrated in FIG. 9(*a*), it is assumed that the second loop 421B and the second low input impedance signal processing circuit 430B are connected. That is, with respect to the connection between the first loop 421A and the first low input impedance signal processing circuit 430A, it is assumed that the second loop 421B and the second low input impedance signal processing circuit 430B are connected in point symmetry with a point 901 illustrated between the sub-coil 410A and the second sub-coil 410B in this figure. Hereinafter, this connection mode is referred to as forward connection.

<Premise 1>

FIG. 10(*a*) illustrates the relationship between a subject, the first sub-coil 410A, the second sub-coil 410B and the direction of a static magnetic field (similar to FIG. 6(*b*)). In this arrangement, the loop plane of a coil is substantially parallel to the plane perpendicular to the static magnetic field direction.

In the case of the forward connection as illustrated in FIG. 9(*a*), since the relationship between the first loop 421A and the ground 490 (reference potential) is equal to the relationship between the second loop 421B and the ground 490, the same voltage is applied and clockwise currents $I_1$ and $I_3$ flow in both. Here, it is assumed that each circuit element is adjusted so that, when the first sub-coil 410A is magnetically coupled to the second sub-coil 410B, the clockwise current $I_1$ flows in the first loop 421A, the counterclockwise current $I_2$ flows in the second loop 421B, and a butterfly current flows in the circuit 601. In this case, a phase difference between the currents $I_1$ and $I_2$ is about 180 degrees (<180 degrees).

In this case, a current mode 471 at alone indicated by a solid line in FIG. 9(*a*) and a current mode 472 at magnetic coupling indicated by a broken line are formed in the second loop 421B. As illustrated in FIG. 9(*a*), in the second loop 421B, the current mode 471 at alone and the current mode 472 at magnetic coupling are almost opposite flows.

FIG. 10(*b*) illustrates the phase of a signal current flowing through the second loop 421B in each of the current modes 471 and 472 at this time. FIG. 10(*b*) is a diagram illustrating a phase in a complex plane. Here, it is assumed that the phase θ1 of the current $I_2$ flowing through the second loop 421B by the first current mode 471 at magnetic coupling is 0 (reference).

As described above, the current mode 472 at magnetic coupling is a counterclockwise current in the second loop 421B. Assuming that the phase θ1 of the current $I_2$ by the first current mode 471 is 0, the phase θ2 of a signal (current $I_3$) produced in the second loop 421B by the current mode 472 at alone is α (about 180 degrees).

Therefore, in the second loop 421B, the directions of these currents ($I_2$ and $I_3$) are substantially opposite. FIG. 10(*c*) illustrates the relationship between the phase of a rotating magnetic field produced on the XY plane of the region of interest of the subject 103 (e.g., the center of the subject 103) by $I_2$ flowing in the second loop 421B and the phase of a rotating magnetic field produced on the XY plane of the same region of interest by $I_3$. Φ1 is the phase of the rotating magnetic field in the region of interest produced by the first current mode by $I_2$, which is the reference phase here. Φ2 is the phase of the rotating magnetic field in the region of interest produced by the second current mode by $I_3$, which is different from Φ1 by about 180 degrees.

In this case, as illustrated in this figure, since the directions of the magnetic fields are substantially opposite, the produced resultant magnetic field is canceled out. That is, from the reciprocity theorem, a current flowing in the input terminal of the second low input impedance signal processing circuit 430B which actually detects a signal is lowered and the reception sensitivity is also lowered.

Therefore, in the first embodiment, as illustrated in FIG. 9(*b*), the connection between the second loop 421B and the second low input impedance signal processing circuit 430B is made to be opposite to the forward connection (hereinafter referred to as backward connection). That is, the connection at both ends of the first parallel capacitor 424B is reversed. In other words, the ground (reference potential) is reversed. As a result, a phase θ22 of the second current mode 472 is inverted (rotated by plus 180 degrees), as illustrated in FIG. 10(*d*).

As illustrated in FIG. 10(*e*), since the phase Φ1 of the rotating magnetic field produced on the XY plane by $I_2$ flowing through the second loop 421B and a phase Φ22 of the rotating magnetic field produced on the XY plane by $I_3$ have substantially the same direction (90 degrees or less in terms of phase difference), the cancellation of magnetic fields is weakened. That is, from the reciprocity theorem, the current flowing in the input terminal of the second low input impedance signal processing circuit 430B which actually detects a signal is increased and the reception sensitivity is improved.

<Premise 2>

FIG. 11(*a*) illustrates the relationship between a subject, the first sub-coil 410A, the second sub-coil 410B and the static magnetic field direction. In this arrangement, the loop plane of a coil is substantially parallel to the plane (x-z plane) in parallel to the static magnetic field direction.

In the case of the forward connection as illustrated in FIG. 9(a), since the relationship between the first loop 421A and the ground 490 (reference potential) is equal to the relationship between the second loop 421B and the ground 490, the same voltage is applied and clockwise currents $I_1$ and $I_3$ flow in both. Here, it is assumed that each circuit element is adjusted so that, when the first sub-coil 410A is magnetically coupled to the second sub-coil 410B, the clockwise current $I_1$ flows in the first loop 421A, the counterclockwise current $I_2$ flows in the second loop 421B, and a butterfly current flows in the circuit 601. In this case, a phase difference between the currents $I_1$ and $I_2$ is about 180 degrees (<180 degrees).

In this case, a current mode 471 at alone indicated by a solid line in FIG. 9(a) and a current mode 472 at magnetic coupling indicated by a broken line are formed in the second loop 421B. As illustrated in FIG. 9(a), in the second loop 421B, the current mode 471 at alone and the current mode 472 at magnetic coupling are almost opposite flows.

Figure 11A:
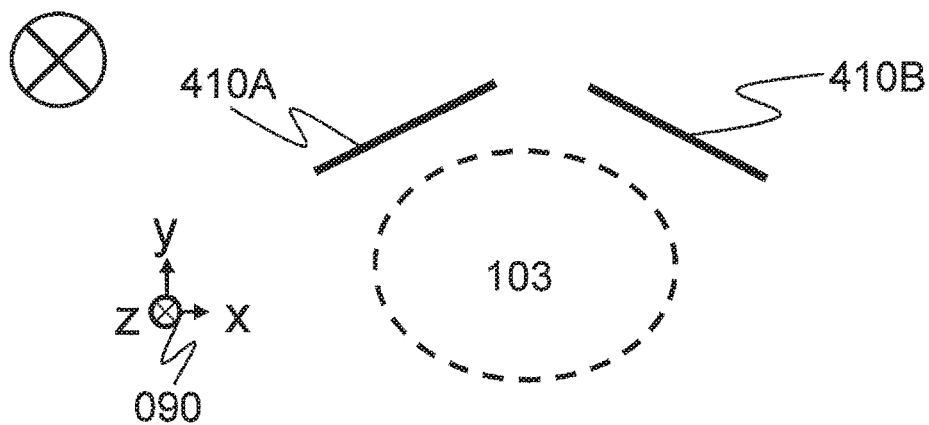
FIGS. 11A to 11C are explanatory views for explaining the phase of a signal generated at an input terminal of the low input impedance signal processing circuit of the first embodiment.
Figure 11B:
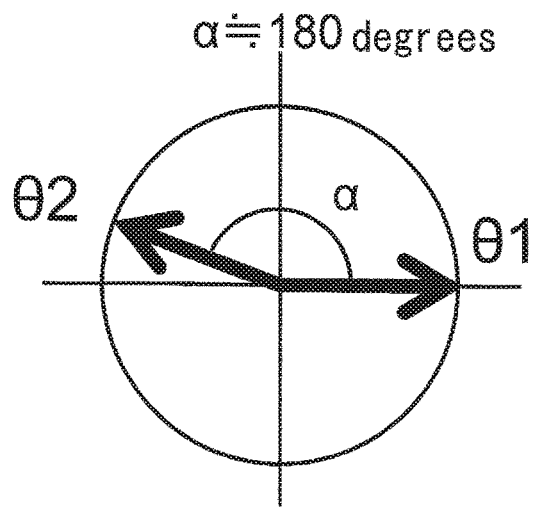

FIG. 11(b) illustrates the phase of a signal (current) produced in the second loop 421B by each of the current modes 471 and 472 at this time. FIG. 11(b) is a diagram illustrating a phase in a complex plane. Here, it is assumed that the phase θ1 of the signal (current $I_2$) produced in the second loop 421B by the first current mode 471 at magnetic coupling is 0 (reference).

As described above, the current mode 472 at magnetic coupling is a counterclockwise current in the second loop 421B. Assuming that the phase θ1 of the current $I_2$ by the first current mode 471 is 0, the phase θ2 of a signal (current $I_3$) produced in the second loop 421B by the current mode 472 at alone is α (about 180 degrees).

Figure 11C:
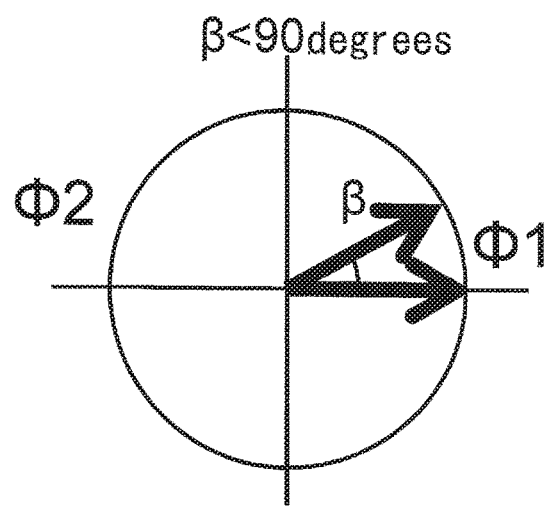

Therefore, in the second loop 421B, the directions of these currents ($I_2$ and $I_3$) are substantially opposite. FIG. 11(c) illustrates the relationship between the direction of a rotating magnetic field produced on the XY plane of the region of interest of the subject 103 (e.g., the center of the subject 103) by $I_2$ flowing in the second loop 421B and the direction of a rotating magnetic field produced on the XY plane of the same region of interest by $I_3$. Φ1 is the phase of the rotating magnetic field produced by the first current mode by $I_2$, which is the reference phase here. Φ2 is the phase of the rotating magnetic field produced by the second current mode by $I_3$, which has substantially the same direction as Φ1 (90 degrees or less).

In this case, as illustrated in this figure, since the directions of the magnetic fields are substantially the same, the produced resultant magnetic field is hardly canceled out. That is, from the reciprocity theorem, a current flowing in the input terminal of the second low input impedance signal processing circuit 430B which actually detects a signal is increased and the reception sensitivity is improved.

In this manner, with the arrangement as illustrated in FIG. 11(a), high sensitivity may be realized at the time of forward connection. That is, when the second loop 421B and the low input impedance signal processing circuit 430B are connected such that the rotating magnetic fields produced on the XY plane of the region of interest by each current mode formed by the subject, the first sub-coil 410A and the second sub-coil 410B are not cancelled each other, signals may be received efficiently and the sensitivity may be improved.

<Premise 3>

Figure 12A:
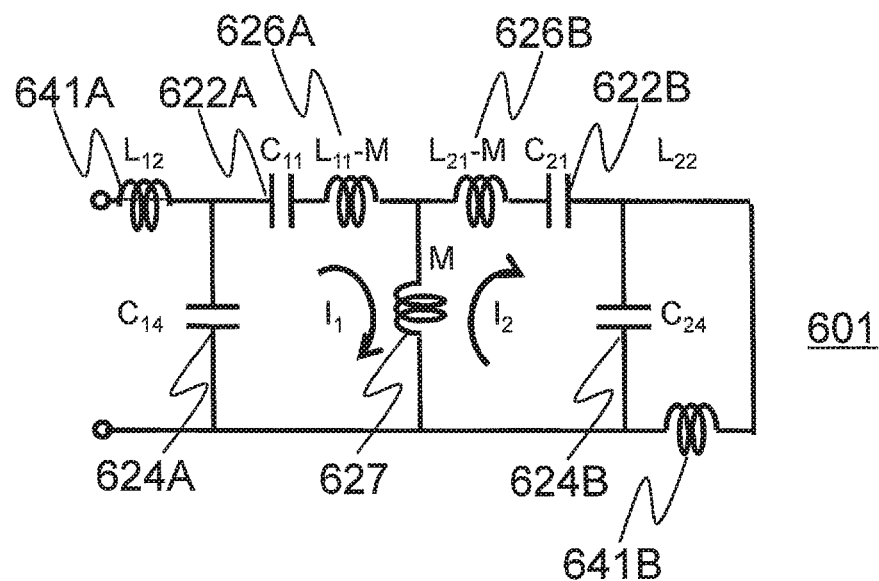
FIGS. 12A and 12B are explanatory views for explaining the direction of a current flowing through the array coil of the first embodiment.
Figure 12B:
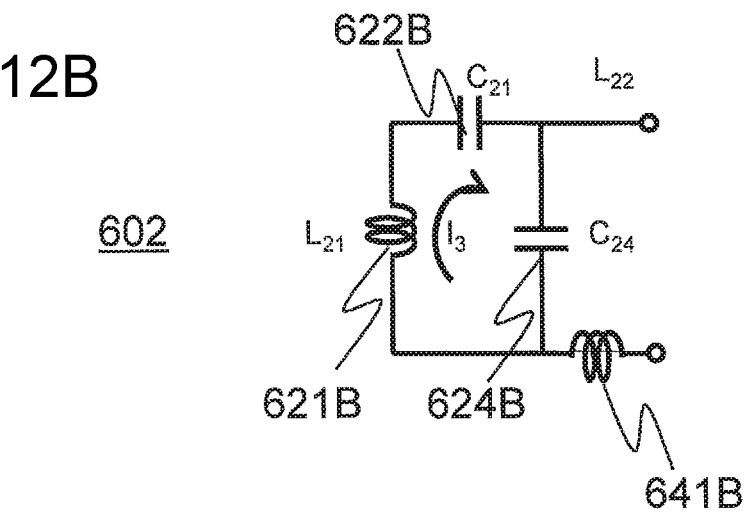

In the case of the forward connection between the second loop 421B and the second low input impedance signal processing circuit 430B, at the time of signal reception, as illustrated in FIGS. 12(a) and 12(b), it is assumed that each circuit element is adjusted so that clockwise currents $I_1$ and $I_3$ flow in both in the first loop 421A and the second loop 421B and a current of approximately plus 90 degrees with respect to the loop flows through each low input impedance signal processing circuit 430. Further, at the time of magnetic coupling, it is assumed that each circuit element is adjusted so that clockwise currents $I_1$ and $I_3$ flow in both in the first loop 421A and the second loop 421B and a current, which is regarded as a current of a surface coil corresponding to a combination of the first loop 421A and the second loop 421B, flows in the circuit 601. In this case, the phase difference between the currents $I_1$ and $I_2$ is approximately 0 degrees (<90 degrees).

Figure 13A:
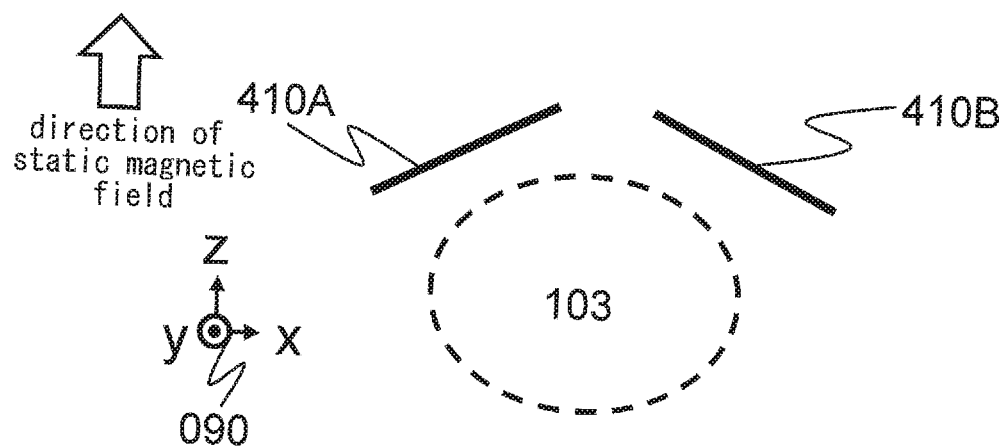
FIGS. 13A to 13C are explanatory views for explaining the phase of a signal generated at an input terminal of the low input impedance signal processing circuit of the first embodiment.

FIG. 13(a) illustrates the relationship between a subject, the first sub-coil 410A, the second sub-coil 410B and the static magnetic field direction. In this arrangement, similarly to FIG. 11(a), the loop plane of a coil is substantially parallel to the plane perpendicular to the static magnetic field direction.

Figure 14:
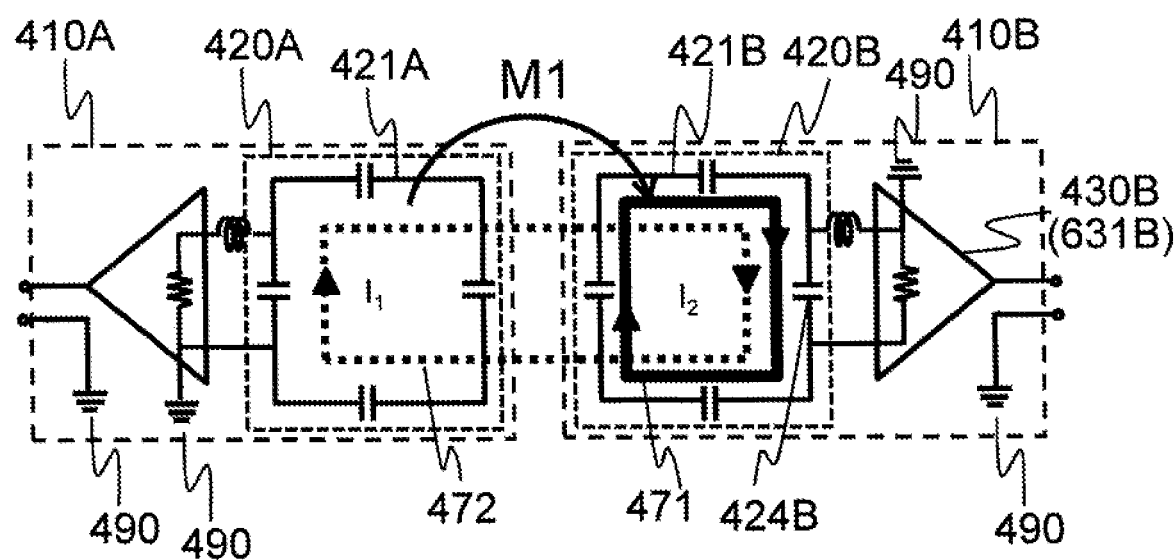
FIG. 14 is an explanatory view for explaining the direction of a current flowing through the array coil of the first embodiment.

In this case, a current mode 471 at alone indicated by a solid line in FIG. 14 and a current mode 472 at magnetic coupling indicated by a broken line are formed in the second loop 421B. As illustrated in FIG. 14, in the second loop 421B, the current mode 471 at alone and the current mode 472 at magnetic coupling have substantially the same direction of flow.

Figure 13B:
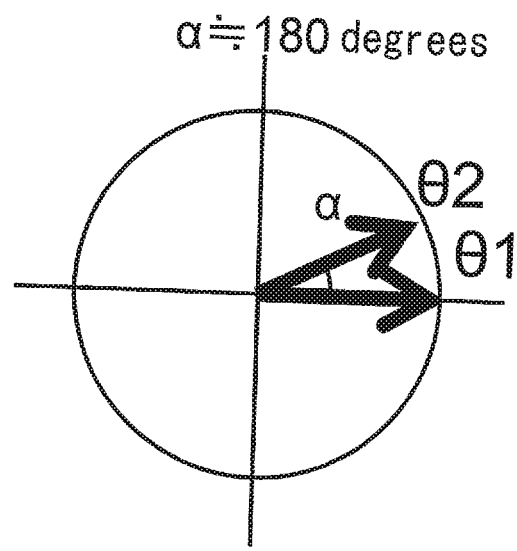

FIG. 13(b) illustrates the phase of a current flowing in the second loop 421B by each of the current modes 471 and 472 at this time. FIG. 13(b) is a diagram illustrating a phase in a complex plane. Here, it is assumed that the phase θ1 of the current $I_2$ flowing in the second loop 421B by the first current mode 471 at magnetic coupling is 0 (reference).

As described above, assuming that the current mode 472 at magnetic coupling is a clockwise current in the second loop 421B and that the phase θ1 of the current $I_2$ by the first current mode 471 is 0, the phase θ2 of the current $I_3$ flowing in the second loop 421B by the current mode 472 at alone is α (about 0 degree).

As described above, the current mode 472 at magnetic coupling is a clockwise current in the second loop 421B. Assuming that the phase θ1 of the current $I_2$ by the first current mode 471 is 0, the phase θ2 of a signal (current $I_3$) produced in the second loop 421B by the current mode 472 at alone is α (about 0 degree).

Figure 13C:
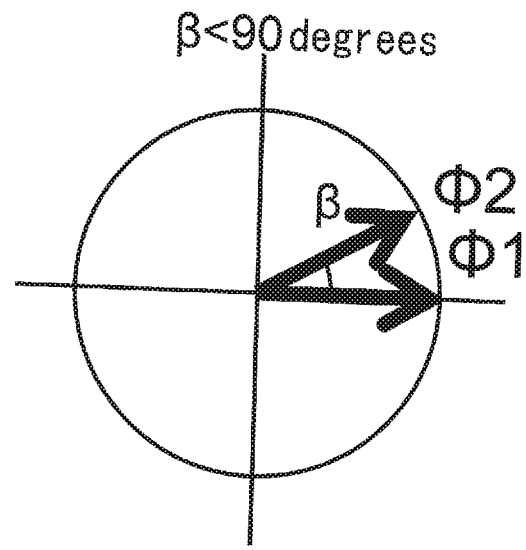

Therefore, in the second loop 421B, the directions of these currents ($I_2$ and $I_3$) are substantially the same. FIG. 13(c) illustrates the relationship between the direction of a rotating magnetic field produced on the XY plane of the region of interest of the subject 103 (e.g., the center of the subject 103) by $I_2$ flowing in the second loop 421B and the direction of a rotating magnetic field produced on the XY plane of the same region of interest by $I_3$. Φ1 is the phase of the rotating magnetic field produced by the first current mode by $I_2$, which is the reference phase here. Φ2 is the phase of the rotating magnetic field produced by the second current mode by $I_3$, which has substantially the same direction as Φ1 (90 degrees or less).

In this case, as illustrated in this figure, since the directions of the magnetic fields are substantially the same, the produced resultant magnetic field is hardly canceled out. That is, from the reciprocity theorem, a current flowing in the input terminal of the second low input impedance signal processing circuit 430B which actually detects a signal is increased and the reception sensitivity is improved.

In this manner, with the arrangement as illustrated in FIG. 13(a), high sensitivity may be realized at the time of forward connection. That is, when the second loop 421B and the low input impedance signal processing circuit 430B are connected such that the rotating magnetic fields produced on the XY plane of the region of interest by each current mode formed by the subject, the first sub-coil 410A and the second sub-coil 410B are not cancelled each other, signals may be received efficiently and the sensitivity may be improved.

By arranging and connecting circuit elements and adjusting the values thereof as described above, each sub-coil 410 can efficiently receive a nuclear magnetic resonance signal to be detected.

In addition, at the time of signal reception, the first sub-coil 410A is magnetically coupled to the second sub-coil 410B, as illustrated in FIGS. 8(b) and 12(a), and functions as the sub-coil 410 having a wide and deep sensitivity region. Further, by adjusting the value of the capacitor or the inductor of the magnetic coupling adjusting part 441, it is possible to change the magnitude of the magnetic coupling and adjust a sensitivity distribution.

In the meantime, the second sub-coil 410B does not magnetically couple with the first sub-coil 410A, but functions as the sub-coil 410 alone as illustrated in FIGS. 8(c) and 12(b). Therefore, at the time of signal reception, the first sub-coil 410A and the second sub-coil 410B exhibit different sensitivity distributions for an imaging region. Thus, they function as a multi-channel coil.

Adjustment Example

Hereinafter, an adjustment procedure of each circuit element of the first embodiment will be described with a specific example. Here, a case where the array coil 400 is adjusted to resonate at a magnetic resonance frequency 124 MHz of hydrogen nuclei ($f_0$=124 MHz) will be described by way of an example.

In addition, as illustrated in FIG. 8(b), when the first sub-coil 410A is magnetically coupled to the second sub-coil 410B, the loop 421A and the loop 421B are adjusted such that a clockwise current flows in the first loop 421A and a counterclockwise current flows in the second loop 421B, thereby to form a current path such as a butterfly coil effectively. Specifically, in the arrangement of the loop 421A and the loop 421B of the first embodiment, the resonance frequency of the parallel resonance circuit ($L_{22}C_{24}$ resonance circuit) formed by the inductor 641B and the parallel capacitor 624B is set to be smaller than $f_0$.

First, each circuit element of the second sub-coil 410B is adjusted. At this time, the loop coil part 420A of the first sub-coil 410A is in an open state.

The values of the capacitance $C_{21}$ of the series capacitor 622B and the capacitance $C_{24}$ of the parallel capacitor 624B are adjusted. Here, these values are adjusted such that the equivalent circuit 602 illustrated in FIG. 8(c) resonates at 124 MHz and the impedance at both ends of the series circuit of the inductor 641B and the parallel capacitor 624B becomes 50Ω.

At the same time, the value $L_{22}$ of the inductor 641B and the value $C_{24}$ of the parallel capacitor 624B are adjusted so as to satisfy the equation (9).

At this time, in order to make a current flow at the time of magnetic coupling as described above, the values of $L_{22}$ and $C_{24}$ are determined so that the parallel resonance circuit formed by the adjustment inductor 641B and the parallel capacitor 624B operates as a capacitor. These values are adjusted based on the characteristic principle of a parallel resonance circuit, as will be described later. Specifically, these values are adjusted so that the resonance frequency of the parallel resonance circuit ($L_{22}C_{24}$ resonance circuit)

formed by the inductor 641B and the parallel capacitor 624B has a value smaller than. The value smaller than $f_0$ is, for example, 90 MHz.

Next, each circuit element of the first sub-coil 410A is adjusted. At this time, it is assumed that each circuit element of the second sub-coil 410B has already been adjusted as described above.

Here, the value $C_{11}$ of the series capacitor 622A and the value $C_{14}$ of the parallel capacitor 624A are adjusted such that the equivalent circuit 601 illustrated in FIG. 8(b) resonates at 124 MHz and the impedance at both ends of the series circuit of the inductor 641A and the parallel capacitor 624A (C14) becomes 50Ω.

At the same time, in order to prevent the second sub-coil 410B from magnetically coupling with the first sub-coil 410A, the value $L_{12}$ of the adjustment inductor 641A and the value $C_{14}$ of the parallel capacitor 624A are adjusted so as to satisfy the equation (10) at the same time. Accordingly, when looked at from the second sub-coil 410B, the first sub-coil 410A may be regarded as a circuit in which high impedance is inserted in the first loop 421A. Accordingly, the second sub-coil 410B does not magnetically couple with the first sub-coil 410A.

The adjustment of the first sub-coil 410A and the second sub-coil 410B may be repeated several times as necessary.

When the value smaller than $f_0$ is 90 MHz, the values of the parameters adjusted by the above adjustment are, for example, $C_{11}$=7.7 pF, $C_{14}$=148 pF, $C_{21}$=98 pF, $C_{24}$=7.9 pF, $L_{12}$=11 nH and $L_{22}$=26 nH.

By performing the adjustment in this manner, the array coil 400 of the first embodiment resonates at the nuclear magnetic resonance frequency and receives the nuclear magnetic resonance signal. Further, by magnetically coupling the two sub-coils 410A and 410B each other, the size of the coil is effectively enlarged to expand the sensitivity region. Then, a current distribution such as a butterfly coil or a large surface coil is constructed to form a sensitivity distribution, which cannot be obtained by only two small surface coils, to obtain a signal with high efficiency (high sensitivity). That is, the first embodiment may be used to increase the sensitivity even in a region where it was difficult to increase the sensitivity due to the relationship between the static magnetic field direction and the magnetic field of an RF coil, such as the subject's head top in a tunnel type MRI (horizontal magnetic field type MRI apparatus 100), the abdominal front side in an open type MRI (vertical magnetic field type MRI apparatus 101), etc.

Experimental Results

In the first embodiment, as described above, both of the current mode at magnetic coupling and the current mode at alone are generated in one loop 421. Then, the connection between the loop 421 and the low input impedance signal processing circuit 430 is determined so that the phase of a rotating magnetic field produced by the two current modes in a region of interest of the subject is less than 90 degrees.

The experimental results of the effects achieved by this connection are illustrated below.

Figure 15A:
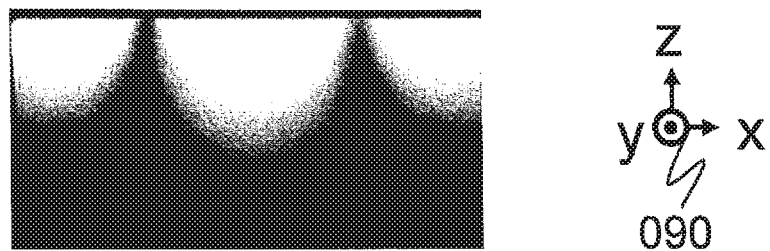
FIGS. 15A to 15C are explanatory views for explaining results of actual measurement of an echo signal in an MRI apparatus using a trial array coil of the first embodiment.
Figure 15B:
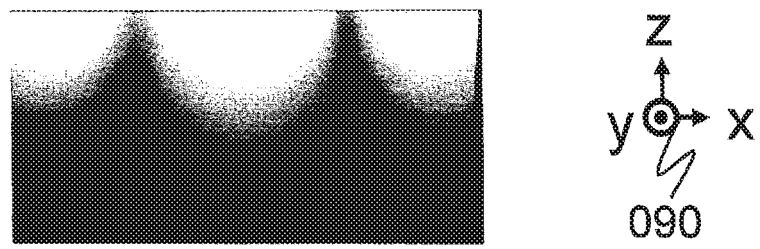
Figure 15C:
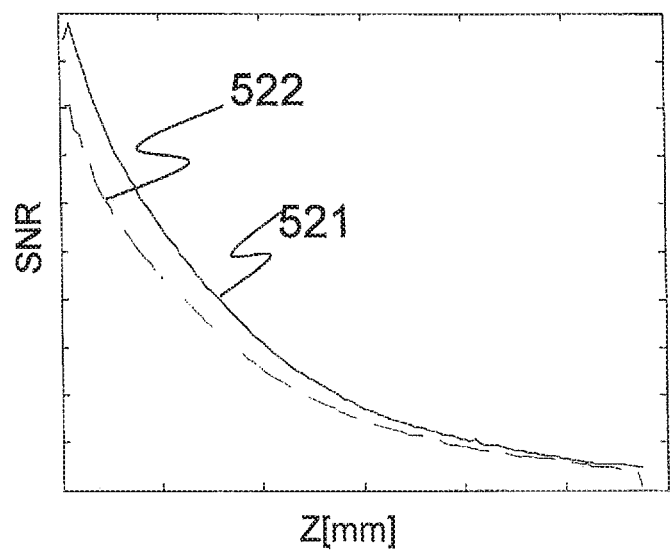

FIGS. 15(a) to 15(c) show the results of actual measurement of a magnetic resonance signal in the MRI apparatus 100 using a trial array coil 400. Here, as the array coil 400, two square sub-coils 410 each having a side of 100 mm were prepared and used as the first sub-coil 410A and the second sub-coil 410B. Then, the first sub-coil 410A and the second sub-coil 410B were arranged under the above conditions and each circuit element was adjusted under the above conditions. A water phantom simulating the human body was used as the subject 103.

FIG. 15(*a*) illustrates an experimental result of water phantom imaging when the second low input impedance signal processing circuit (low input preamplifier) 430B (631B) is connected to the ground 490, as described above. That is, this figure illustrates a result of connection between the coil loop 420 and the low input impedance signal processing circuit 430 so that a phase difference between rotating magnetic fields produced in a region of interest of the subject by the current mode 471 at alone and the current mode 472 at magnetic coupling in the second sub-coil 410B is less than 90 degrees.

FIG. 15(*b*) illustrates a result of connection between the coil loop 420 and the low input impedance signal processing circuit 430 so that a phase difference between rotating magnetic fields produced in a region of interest of the subject by the current mode 471 at alone and the current mode 472 at magnetic coupling is more than 90 degrees.

FIG. 15(*c*) illustrates an SNR line profile in the z direction at the center of the x direction in each of FIGS. 15(*a*) and 15(*b*). A solid line 521 and a broken line 522 indicate the same line profile in FIGS. 15(*a*) and 15(*b*), respectively.

As can be seen from these figures, by making the connection such that the phase difference between the rotating magnetic fields produced by both current modes is less than 90 degrees, the cancellation of the produced magnetic fields may be weakened to realize a wider sensitivity region and a higher SNR in a region of the subject 103.

As described above, the MRI apparatus 100 of the first embodiment includes a static magnetic field forming unit (the magnet 110) that forms a static magnetic field, a gradient magnetic field forming unit that forms a gradient magnetic field (the gradient magnetic field power supply 132 and the gradient magnetic field coil 131), an RF magnetic field generating unit (the RF magnetic field generator 152) that generates an RF magnetic field, a transmitting coil (the transmitting RF coil 151) that irradiates a subject with the RF magnetic field, a receiving coil (the receiving RF coil 161) that detects a nuclear magnetic resonance signal, which is an RF signal, from the subject, and an image reconstructing unit (the computer 170) that reconstructs an image from the detected nuclear magnetic resonance signal. The transmitting coil 151 and the receiving coil 161 are provided with the magnetic coupling prevention circuits 210 and 220 for preventing the magnetic coupling between the transmitting coil and the receiving coil, respectively.

The array coil 400 used as the receiving coil 161 includes the first sub-coil 410A and the second sub-coil 410B, each of which has the loop coil part 420 that is formed of a conductor and detects an RF signal, and the signal processing circuit 430 that receives the RF signal detected by the loop coil part 420. The loop coil part 420A of the first sub-coil 410A and the loop coil part 420B of the second sub-coil 410B are adjusted so as to be magnetically coupled to each other, and are arranged at positions at which an RF magnetic field produced between the first sub-coil 410A and the second sub-coil 410B may be detected as the RF signal, respectively. The loop coil part 420 and the signal processing circuit 430 are connected such that the phase difference between the first rotating magnetic field produced by the loop coil part 420 alone in a region of interest of the subject and the second rotating magnetic field produced in the region of interest of the subject by magnetic coupling of the loop coil part 420 is less than 90 degrees.

In this manner, with the array coil 400 used in the receiving RF coil 161 of the first embodiment, it is possible to prevent the rotating magnetic field generated by the sub-coil 410 from being cancelled out due to the influence of a current flowing in adjacent another sub-coil 410 when a magnetic coupling occurs.

Generally, when the phases of currents flowing in both sub-coils are different from each other, rotating magnetic fields in opposite directions are generated in both sub-coils, and the sensitivity of one sub-coil may be increased by the rotating magnetic fields, while the sensitivity of the other sub-coil may be decreased by the rotating magnetic fields. Therefore, the expected sensitivity may not be obtained even when signals are combined using a plurality of sub-coils. However, according to the first embodiment, it is possible to obtain the desired sensitivity since a rotating magnetic field can be produced efficiently in only one direction.

In this manner, according to the first embodiment, by determining the connection mode of the low input impedance signal processing circuit 430 so that the phase difference of the produced rotating magnetic fields is less than 90 degrees, the two sub-coils 410 are tuned to enhance a signal. Thus, according to the first embodiment, a signal may be acquired with high efficiency.

Therefore, according to the first embodiment, even when the receiving RF coil 161 is a multi-channel array coil, it is possible to suppress the influence of a current flowing through other sub-coils to keep the desired sensitivity. Accordingly, it is possible to obtain the high sensitivity and the wide range of the sensitivity region, which may be achieved only by the multi-channel array coil, and to obtain a high quality image.

In addition, since the phase difference between signals detected by the respective sub-coils 410 is small, even when interference occurs due to imperfections of the device or the like until the signals are output from the low input impedance signal processing circuit 430 and detected by the receiver 162, the signals are less likely to be cancelled out each other. As a result, signal reduction is decreased and the SNR of the image is increased.

In addition, the first sub-coil 410A and the second sub-coil 410B have different sensitivity distributions for a imaging region. Therefore, the array coil 400 of the first embodiment maintains multi-channel characteristics such that it is composed of a plurality of coils having different sensitivity distributions within the imaging region, enabling high-speed imaging.

One terminal on the output side of the signal processing circuit 430 may be grounded and the loop coil part 420 may be a parallel resonance circuit.

Typically, when RF coils having the same resonance characteristics are arranged close to each other, they interfere with each other by magnetic coupling. Since the performance of the RF coils is deteriorated due to the magnetic coupling, it has been conventionally devised to reduce this magnetic coupling as much as possible. For example, when the magnetic coupling is reduced by arranging coil loops of adjacent sub-coils such that some coil loops overlap each other, this is a major restriction on the arrangement of sub-coils.

In order to minimize remaining magnetic coupling, it is also possible to apply a plurality of magnetic coupling removing units. However, the magnetic coupling removing unit itself actually has some loss. Therefore, applying the plurality of magnetic coupling removing unit causes not only magnetic coupling removal but also reduction of sensitivity of the array coil. In the case of a super multi-channel array coil, it is necessary to remove magnetic coupling with a plurality of sub-coils, which complicates the configuration.

However, according to the first embodiment, in accordance with the magnetic coupling, the direction of grounding is adjusted so that the signals of the respective modes are not cancelled with each other in the low input impedance signal processing circuit 430 serving as a signal detecting unit. That is, by merely changing the connection between the loop coil part 420 and the signal processing circuit 430, the influence by the magnetic coupling is removed. That is, according to the first embodiment, the above-described effects may be realized with a simple configuration.

In the first sub-coil 410A, the resonance frequency of the first sub-coil 410A alone is different from a reception frequency which is the frequency of the RF signal to be received. The first sub-coil 410A may be arranged and adjusted so that, when the first sub-coil 410A is magnetically coupled to the second sub-coil 410B, a circulating current path is formed in the loop 421A of the loop coil part 420A of the first sub-coil 410A and the loop 421B of the loop coil part 420B of the second sub-coil 410B and, the first sub-coil 410A resonates at the reception frequency.

Further, the first sub-coil 410A and the second sub-coil 410B each include the magnetic coupling adjusting part 441 for connecting the loop coil part 420 and the signal processing circuit 430. The loop coil part 420 includes the series capacitor 422 inserted in series with the inductor component of the loop 421, and the parallel capacitor 424 inserted in parallel to the inductor component to make the loop coil part a parallel resonance circuit. The magnetic coupling adjusting part 441 includes at least one of a capacitor and an inductor as an adjustment circuit element. The first sub-coil 410A and the second sub-coil 410B may be adjusted by the adjustment circuit element, the series capacitor and the parallel capacitor.

In addition, the first sub-coil and the second sub-coil may be arranged in substantially the same plane.

In general, as sub-coils constituting an array coil become smaller due to multi-channelization, the depth of the entire sensitivity region becomes narrower in an array coil which is a set of sub-coils having a narrow sensitivity region. Therefore, the depth sensitivity of a super multi-channel array coil developed for high-speed imaging is lower than that of an array coil composed of fewer channels. Therefore, it is difficult to obtain a clean image in the deep portion of the subject.

In general, a multi-channel array coil is arranged such that a surface coil covers the subject. However, when portions where a rotating magnetic field generated by one sub-coil constituting the array coil has substantially the same direction as a rotating magnetic field formed by a static magnetic field (e.g., the head top of the subject in a tunnel type MRI where the static magnetic field direction is horizontal to the body axis direction of the subject, the abdominal front or the back in an open type MRI where the static magnetic field direction is perpendicular to the body axis direction of the subject, etc.) are imaged, it is difficult to capture the rotating magnetic field, which results in poor efficiency of signal reception. In this case, even when the number of sub-coils is increased for multi-channelization, the effective sensitivity hardly increases.

However, the array coil 400 of the first embodiment arranged and adjusted as described above tunes to the magnetic resonance frequency $f_0$. In addition, at the time of signal reception, the first sub-coil 410A can share the loop coil parts 420A and 420B with the second sub-coil 410B to widen a sensitivity region to detect a signal, and the second sub-coil 410B can detect the signal with high sensitivity without magnetic coupling with the first sub-coil 410A. In this manner, with the array coil 400 of the first embodiment, a sensitivity distribution that cannot be obtained by two small surface coils may be formed to acquire a signal with high efficiency (high sensitivity).

In addition, the first sub-coil 410A and the second sub-coil 410B have different sensitivity distributions for an imaging region. Therefore, the array coil 400 of the first embodiment maintains multi-channel characteristics that it is constituted by a plurality of coils having different sensitivity distributions within the imaging region, enabling high-speed imaging.

In this manner, with the array coil 400 of the first embodiment, it is possible to achieve both of multi-channel and wide and deep sensitivity regions. In addition, the multi-channel, the wide sensitivity region and high sensitivity are realized by arrangement of circuit elements and adjustment of values thereof. Therefore, the configuration is not complicated. Further, by using the array coil 400 as the receiving RF coil 161, the MRI apparatus of the first embodiment may obtain a high quality image at a high speed.

<Another Example of Mutual Inductance Adjustment>

In the first embodiment, the magnitude of the mutual inductance M is adjusted according to the positional relationship between the first sub-coil 410A and the second sub-coil 410B at the time of arrangement. However, the method of adjusting the magnitude of the mutual inductance M is not limited thereto.

Figure 16:
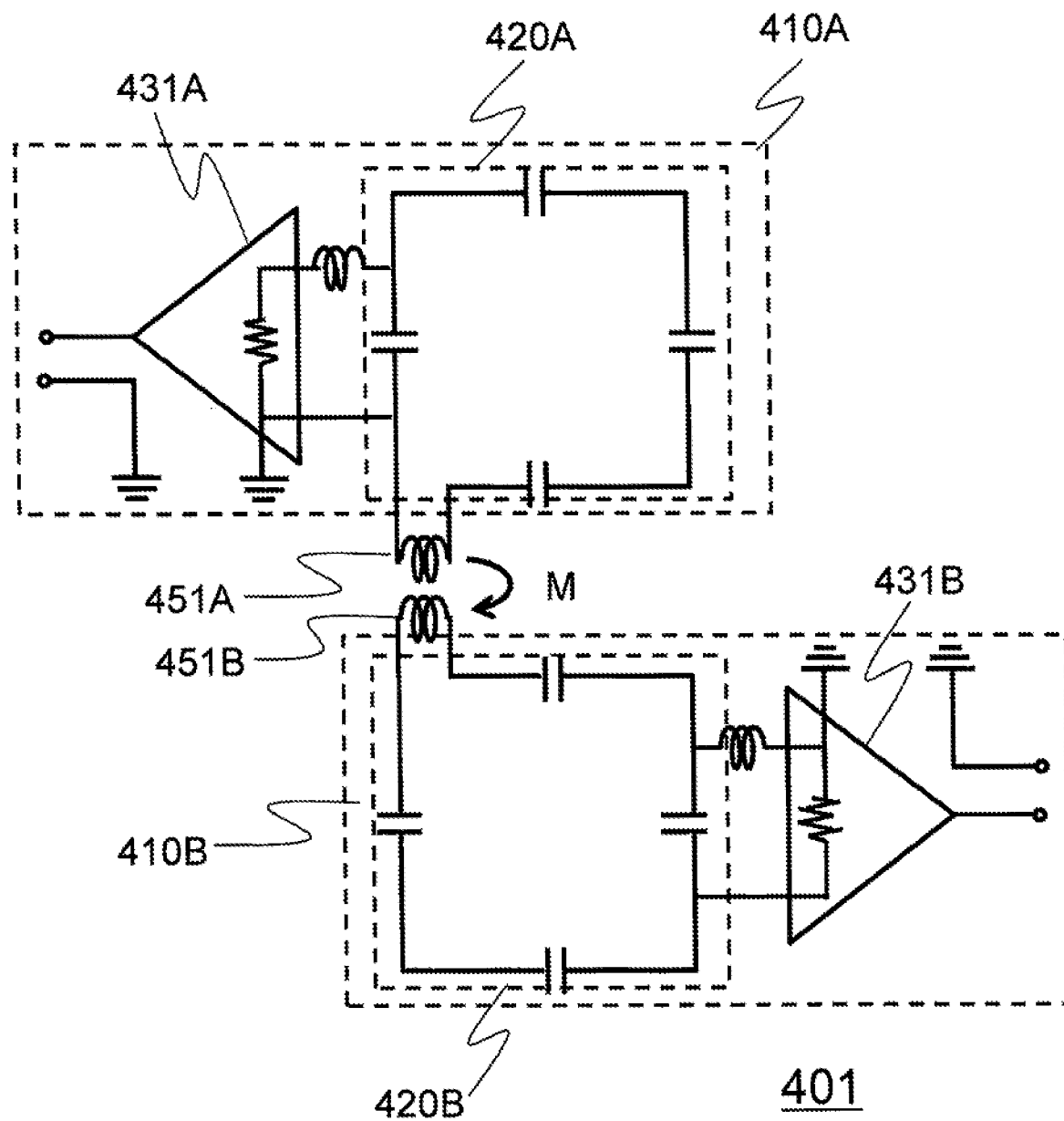
FIG. 16 is an explanatory view for explaining an array coil according to a modification of the first embodiment.

For example, as illustrated in FIG. 16, coupling inductors 451A and 451B may be arranged in a part of each of the loops 421A and 421B, respectively, and may be used to adjust magnetic coupling.

That is, the first sub-coil 410A further includes the first coupling inductor 451A and the second sub-coil 410B further includes the second coupling inductor 451B. Then, the first sub-coil 410A and the second sub-coil 410B are magnetically coupled each other by the first coupling inductor 451A and the second coupling inductor 451B.

The coupling inductor 451 may be attached to only one sub-coil 410. The coupling inductor 451 may be used to freely adjust the magnitude of the mutual inductance M irrespective of the arrangement position of both the sub-coils 410.

At this time, as illustrated in FIG. 16, a portion of the loop 421 may be extended and the coupling inductor 451 may be arranged at the head of the extension. With this configuration, even when the two sub-coils 410A and 410B are arranged at relatively distant positions, they may be magnetically coupled each other. Therefore, when the array coil 400 is provided with the coupling inductor 451, constraints on the arrangement position of both the sub-coils 410 are mitigated. For example, when both the sub-coils 410 are arranged at positions separated from each other, a large coil loop as a whole may be constructed, thereby improving the depth sensitivity.

<Another Example of Arrangement Position of Each Sub-Coil>

In the first embodiment, the case where the array coil 400 is arranged on a plane having an angle relatively close to a plane perpendicular to the magnetic field direction is illustrated. However, the arrangement plane is not limited thereto. It is sufficient if the arrangement is such that a rotating magnetic field generated by the array coil 400 in the region of interest in the direction perpendicular to a static magnetic field may be detected or generated more efficiently than each sub-coil 410 alone.

For example, the array coil 400 may be arranged on a plane having an angle close to a plane parallel to the static magnetic field direction. In addition, the first sub-coil 410A may be arranged on a plane perpendicular to the static magnetic field and the second sub-coil 410B may be arranged on a plane horizontal to the static magnetic field. By changing the arrangement angle in this manner, it becomes possible to detect or generate a rotating magnetic field that cannot be realized by the sub-coil 410 alone, thereby making it possible to acquire a magnetic resonance signal with high sensitivity in the region of interest.

In the first embodiment, the case where the first sub-coil 410A and the second sub-coil 410B are arranged on a plane rotated by 20 degrees with respect to the magnetic field vertical plane is illustrated. However, the arrangement angle is not limited thereto. Both of them may be arranged on the same plane, or may be respectively arranged on planes perpendicular to each other, or may be respectively arranged on two different parallel surfaces.

Further, the first sub-coil 410A and the second sub-coil 410B may be arranged such that a rotating magnetic field may be detected or generated efficiently using the phase difference between currents flowing respectively through the loop 421A and the loop 421B.

By changing the arrangement angle, it is possible to optimize the arrangement of the array coil 400, thereby making it possible to acquire a magnetic resonance signal with high sensitivity.

<Another Example of Circuit Element Adjustment>

In the specific example of the above-described adjustment in the first embodiment, 90 MHz is used as a value smaller than $f_0$ (124 MHz), which is used to adjust the resonance frequency of the $L_{22}C_{24}$ resonance circuit. However, the resonance frequency of the $L_{22}C_{24}$ resonance circuit may have different values.

Sensitivity is increased by setting the resonance frequency of the $L_{22}C_{24}$ resonance circuit to a frequency different from $f_0$. The magnitude of the difference between the resonance frequency of the $L_{22}C_{24}$ resonance circuit and $f_0$ is not particularly limited. However, it is desirable that the difference between the resonance frequency of the $L_{22}C_{24}$ resonance circuit and $f_0$ be different by 10% or more.

That is, the array coil 400 of the first embodiment can increase the sensitivity by adjusting the $L_{22}C_{24}$ resonance circuit to a frequency different from $f_0$ (124 MHz) and actively coupling the two sub-coils 410.

Further, each circuit element may be adjusted at the resonance frequency of the $L_{22}C_{24}$ resonance circuit set to a frequency higher than $f_0$. Such adjustment allows clockwise circulating currents to flow respectively through the first loop 421A and the second loop 421B, thereby allowing the first loop 421A and the second loop 421B to form a current distribution like a large surface coil. Even in this case, the sensitivity of the array coil 400 may be improved by changing the resonance frequency and changing the coupling amount, as in the case of setting the resonance frequency to be lower than $f_0$.

When each loop 421 is arranged such that the positive and negative signs of the coupling coefficient between the first loop 421A and the second loop 421B are opposite to those in the first embodiment, the relationship between the resonance frequency and the current flow is reversed. That is, when the resonance frequency of the $L_{22}C_{24}$ resonance circuit is larger than $f_0$ (124 MHz), a current path like a butterfly coil is effectively formed, whereas, when it is smaller than $f_0$, a current distribution like a large surface coil is effectively formed.

Thus, there is no serious restriction on the resonance frequency of the $L_{22}C_{24}$ resonance circuit at the time of adjustment of each circuit element. Therefore, the array coil 400 of the first embodiment has a high degree of freedom in designing the loop 421.

<Another Example of Size and Shape of Each Sub-Coil>

In the first embodiment, loops of the same size and shape are used as the first loop 421A and the second loop 421B. However, both of them may have different shapes and different sizes.

By using the loops 421 of different shapes and sizes, the degree of freedom of an arrangement pattern is increased. By mitigating the constraints on the shape and/or size of the loops 421, it is easier to adjust the magnitude of magnetic coupling, thereby improving the sensitivity.

In the first embodiment, coils having the same shape are used for the first sub-coil 410A and the second sub-coil 410B. However, combinations of shapes and sizes thereof are not particularly limited but may be different. By combining different shapes thereof, it is possible to realize an optimal coil suitable for the subject 103. It is also possible to adjust the strength of magnetic coupling.

In addition, three capacitors are inserted in the loop 421 of the loop coil part 420, but the present invention is not limited thereto. At least one or more may be inserted.

<Modification of Shape of Coil Part>

In the first embodiment, the shape of the loop 421 of each sub-coil 410 has been described by taking as an example a rectangular or circular single loop on a substantial plane. However, the shape of the loop 421 is not limited thereto. It is sufficient if an equivalent circuit thereof is the same as the equivalent circuit 600.

Figure 17A:
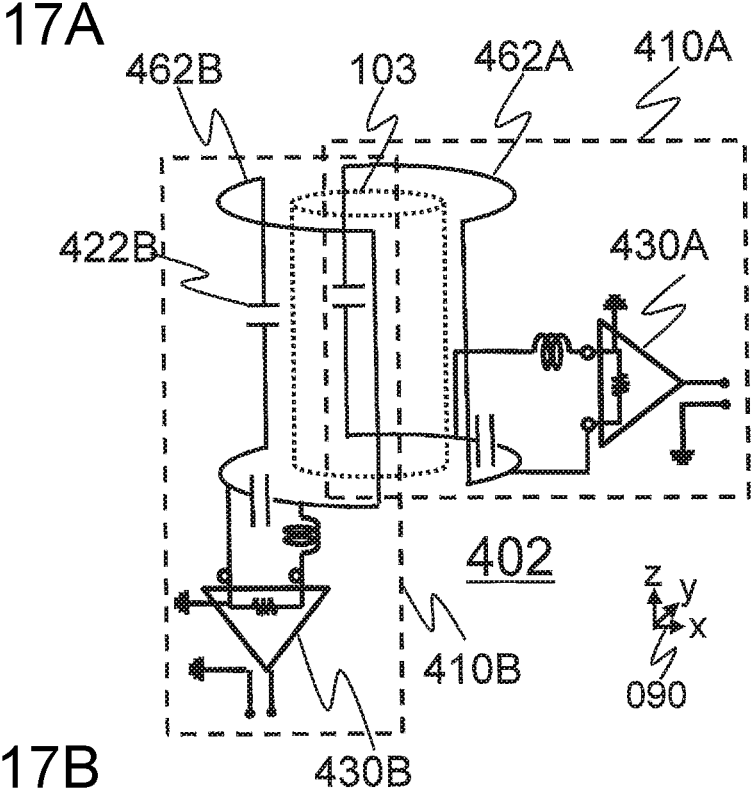
FIGS. 17A and 17B are explanatory views for explaining an array coil of a modification of the first embodiment.

For example, as illustrated in FIG. 17(a), the first loop 462A and the second loop 462B may have a saddle shape in which they are cylindrically arranged to face each other. FIG. 17(a) illustrates an array coil (saddle type array coil) 402 having a saddle loop. In the figure, the z-axis direction of the coordinate system 090 is the static magnetic field direction.

Figure 17B:
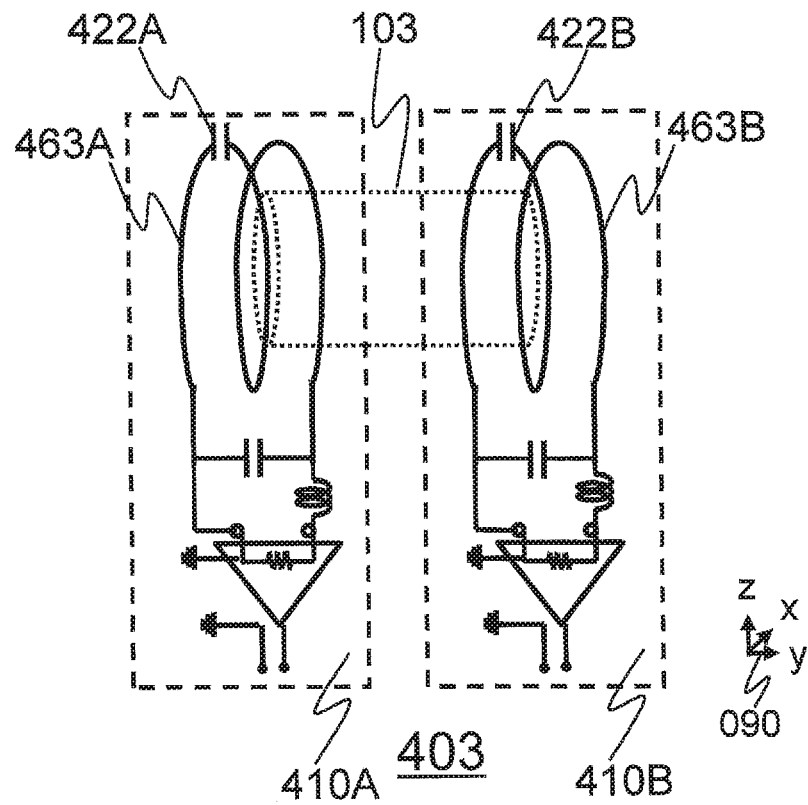

As illustrated in FIG. 17(b), the first loop 463A and the second loop 463B may have a solenoid coil shape and may be arranged adjacent to each other. FIG. 17(b) illustrates an array coil (solenoid type array coil) 403 having a solenoid type loop. In the figure, the z-axis direction of the coordinate system 090 is the static magnetic field direction.

Figure 18:
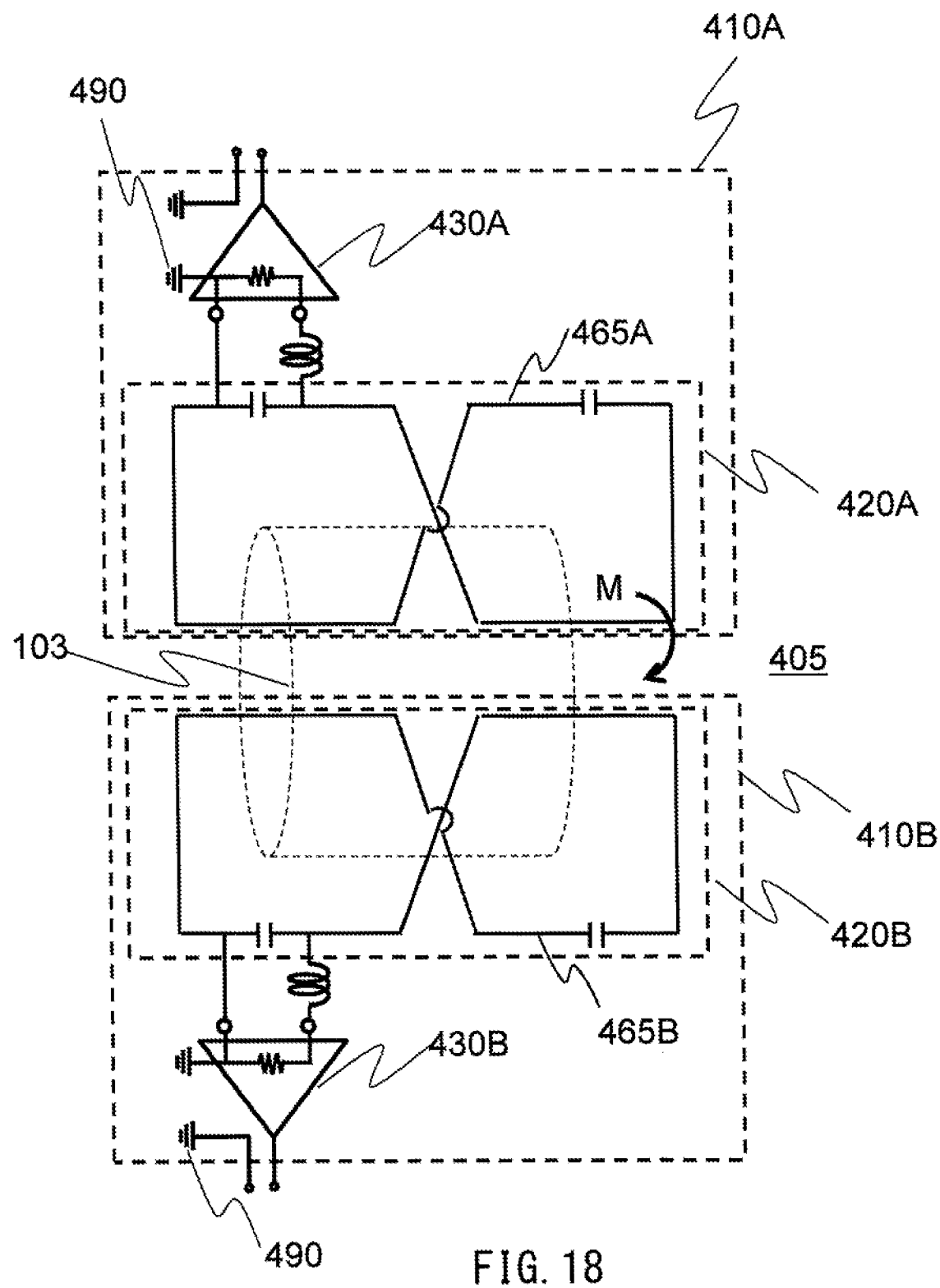
FIG. 18 is an explanatory view for explaining an array coil according to a modification of the first embodiment.

Further, as illustrated in an array coil 405 in FIG. 18, the first loop 465A and the second loop 465B have a butterfly shape and may be arranged adjacent to each other.

Since the shape and mutual inductance of the array coils 402, 403 and 405 are different from those of the array coil 400, the values of the parallel capacitor, the series capacitor and the adjustment inductor are adjusted accordingly. The adjustment is made so as to satisfy the equations (7) to (10) as described above.

Since the saddle type array coil 402, the solenoid type array coil 403 and the butterfly type array coil 405 are represented by the equivalent circuit 600, the operation principle thereof is the same as that of the array coil 400 of the first embodiment. That is, the loops 462A, 463A and 465A of the first sub-coil 410A operate in conjunction with the loops 462B, 463B and 465B of the second sub-coil 410B, respectively. In the meantime, the second sub-coil 410B operates as a single body.

Since the adjustment is performed as described above, each of the sub-coils 410 constituting the array coil 400 has sensitivity to a nuclear magnetic resonance signal to be detected. In addition, since the loops 462A, 463A and 465A of the first sub-coil 410A are coupled to the loops 462B, 463B and 465B of the second sub-coil 410B by magnetic coupling, they may be regarded as a large coil loop and a sensitivity range is expanded. In addition, the second sub-coil 410B does not couple with the first sub-coil 410A and has a sensitivity region. Therefore, the sensitivity distributions of both sub-coils in an imaging region are different and the number of channels may be maintained. Accordingly, it is possible to realize the array coils 402, 403 and 405 having a wide sensitivity region while maintaining the number of channels.

Furthermore, since the loop 462 of the saddle-shaped array coil 402 has a saddle shape, as illustrated in FIG. 17(a), inspection targets 103 such as the arms, foots, trunk, etc. of the subject are placed in the saddle-shaped loop 462. Accordingly, it is possible to detect a magnetic resonance signal from a region in the depth direction in addition to the surfaces of the inspection targets 103 with high sensitivity.

Even in these modifications, the case where one series capacitor 422 is respectively installed in the loops 462, 463 and 465 is exemplified, but the number of capacitors to be inserted is not particularly limited as in the above embodiment. A plurality of series capacitors may be inserted.

In these modifications, loops of the same shape and size are used for the first loop 462A, 463A and 465A and the second loop 462B, 463B and 465B, respectively. However, the sizes and shapes of both may be different. By using loops of different shapes and sizes for each of the first sub-coil 410A and the second sub-coil 410B, the degree of freedom of an arrangement pattern is increased. In addition, the degree of freedom for adjustment of the magnitude of magnetic coupling is increased.

<Modification of Magnetic Coupling>

In the above embodiment and modification, of the two sub-coils 410, at the time of signal reception, the first sub-coil 410A is magnetically coupled to the second sub-coil 410B, and the second sub-coil 410B is not magnetically coupled to the first sub-coil 410A. However, any of the sub-coils 410 may be configured to be magnetically coupled to the other at the time of signal reception.

That is, the second sub-coil 410B alone has a resonance frequency different from the nuclear magnetic resonance frequency and may be adjusted such that it is magnetically coupled to the first sub-coil 410A to form a circulating current path in each of the first loop 421A and the second loop 421B and resonates at the nuclear magnetic resonance frequency.

Figure 19:
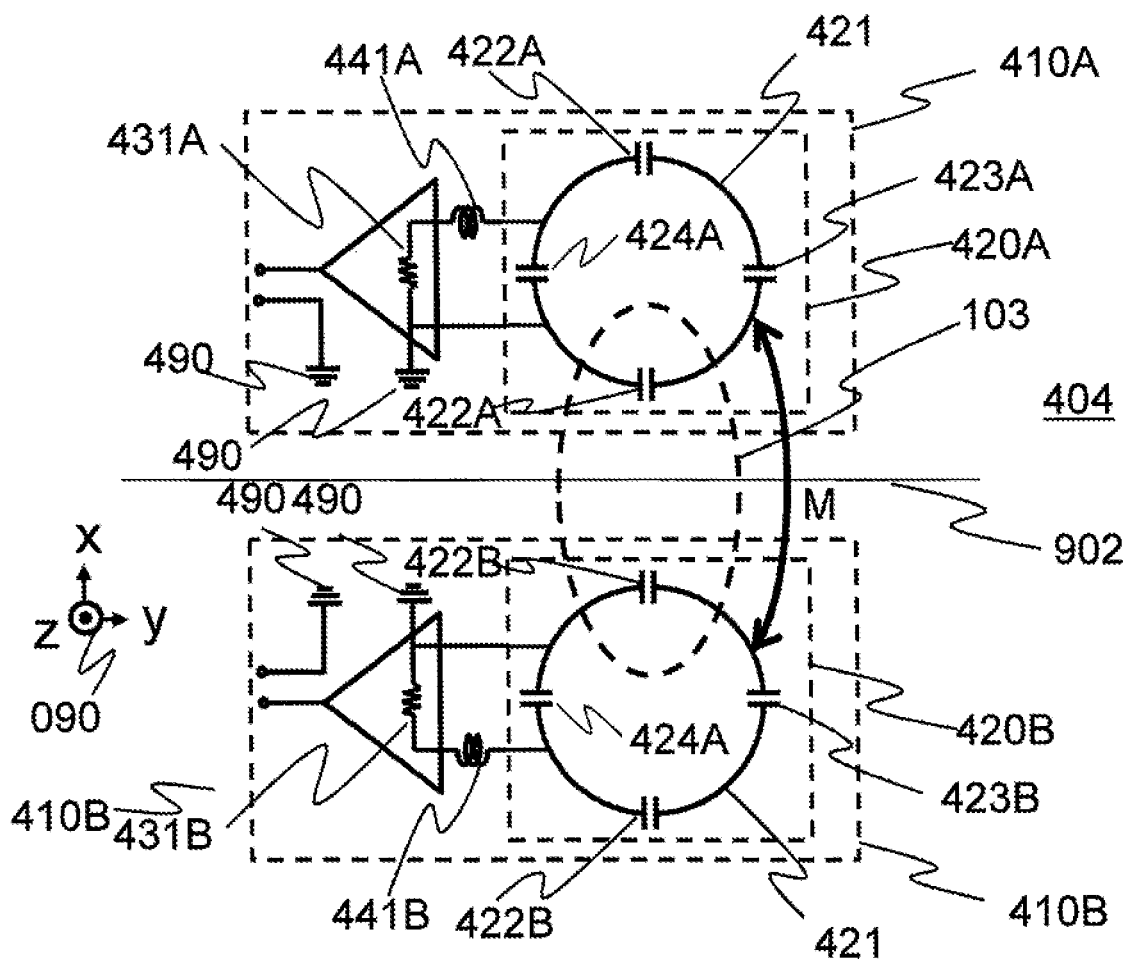
FIG. 19 is an explanatory view for explaining an array coil according to a modification of the first embodiment.
Figure 20A:
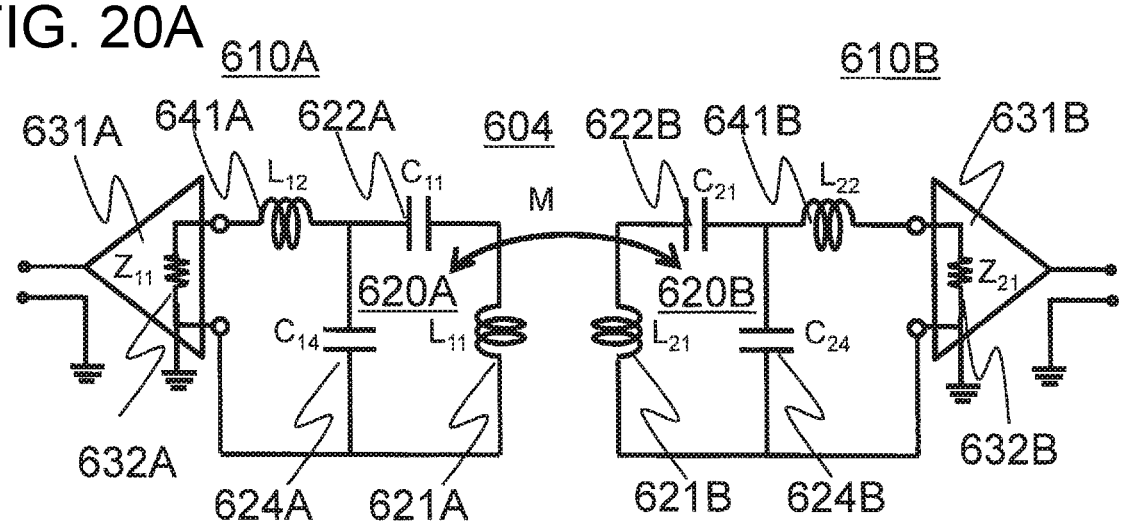
FIGS. 20A to 20C are explanatory views for explaining the operation of the array coil of the modification of the first embodiment.

As illustrated in FIG. 19, an array coil 404 of this modification has the same configuration as the array coil 400 of the first embodiment. However, a method of adjusting the value of each circuit element (the adjustment inductor 441, the series capacitor 422 and the parallel capacitor 424) to be configured is different. Hereinafter, a method of adjusting the value of each circuit element of the array coil 404 will be described using an equivalent circuit 604 of the array coil 404 illustrated in FIG. 20(a).

In the following description, each capacitor and its value, each inductor and its value, and the resonance frequency of each circuit are denoted by the same reference numerals as the equivalent circuit 600 of the first embodiment.

In order to achieve both high sensitivity and multi-channel, each circuit element constituting the array coil 404 is adjusted to satisfy the following equations (11) to (15).

$$f_{11} = f_{22} = f_0 \quad (11)$$

$$f_{10} \neq f_0 \quad (12)$$

$$f_{20} \neq f_0 \quad (13)$$

[Equation 14]

$$\frac{1}{2\pi\sqrt{L_{22}C_{24}}} \neq f_0 \quad (14)$$

$$\frac{1}{2\pi\sqrt{L_{12}C_{14}}} \neq f_0 \quad (15)$$

By adjusting each circuit element according to the equation (14), the resonance frequency of the $L_{22}C_{24}$ resonance circuit of the second sub-coil 410B (610B) is different from the nuclear magnetic resonance frequency $f_0$. Therefore, at the time of signal reception, both ends of the capacitor 424B of the second sub-coil 410B do not have high resistance but are magnetically coupled to the first sub-coil 410A.

Figure 20B:
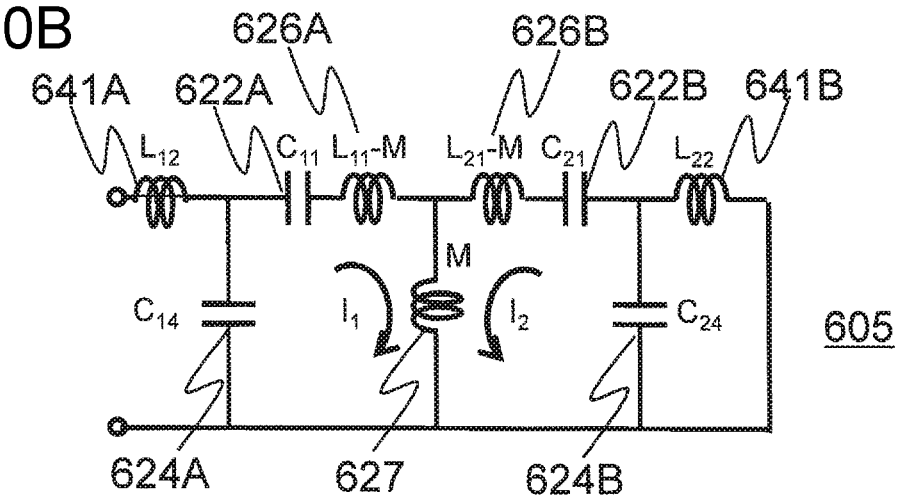

FIG. 20(b) illustrates an equivalent circuit 605 of the first resonance part of the first sub-coil 410A in a state where the first loop coil part 420A and the second loop coil part 420B are magnetically coupled by the above adjustment. That is, at the time of signal reception, the first resonance part of the first sub-coil 410A (610A) becomes a circuit 605 in which the first loop coil part 420A and the second loop coil part 420B are magnetically coupled, as illustrated in FIG. 20(b).

Further, by adjusting each circuit element according to the equation (15), the resonance frequency of the $L_{12}C_{14}$ resonance circuit of the first sub-coil 410A (610A) is different from the nuclear magnetic resonance frequency $f_0$. Therefore, at the time of signal reception, both ends of the capacitor 424A of the first sub-coil 410A do not have high resistance but are magnetically coupled to the second sub-coil 410B.

Figure 20C:
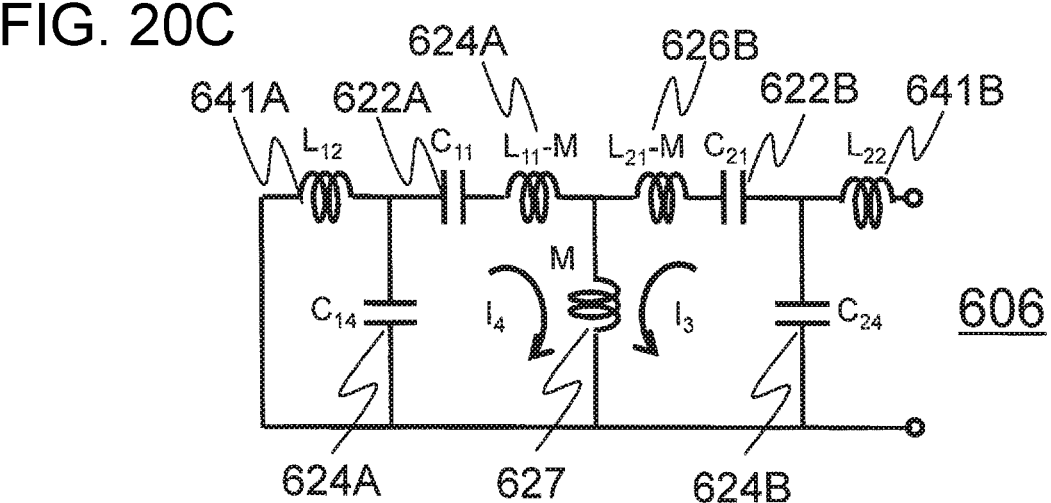

FIG. 20(c) illustrates an equivalent circuit 606 of the second resonance part of the second sub-coil 410B in a state where the first loop coil part 420A and the second loop coil part 420B are magnetically coupled by the above adjustment. That is, at the time of signal reception, the second resonance part of the second sub-coil 410B becomes a circuit 606 in which the first loop coil part 420A and the second loop coil part 420B are magnetically coupled, as illustrated in FIG. 20(c).

In addition, by adjusting each circuit element according to the equations (12) and (13), the individual resonance frequencies $f_{10}$ and $f_{20}$ of the first sub-coil 410A and the second sub-coil 410B are different from the nuclear magnetic resonance frequency $f_0$.

Further, by adjusting each circuit element according to the equation (11), the resonance frequency $f_{11}$ of the first resonance part and the resonance frequency $f_{22}$ of the second resonance part at the time of signal reception become equal to the nuclear magnetic resonance frequency $f_0$. As a result, the sub-coil 410A and the sub-coil 410B may detect a nuclear magnetic resonance signal in a state of being magnetically coupled each other.

At this time, even in this modification, in each sub-coil 410, each loop 421 and the low input impedance signal processing circuit 430 are connected such that the phase difference of rotating magnetic fields generated in the region of interest of the subject at the time of magnetic coupling and at alone is less than 90 degrees.

For example, when the first sub-coil 410 and the second sub-coil 410 are forward-connected together, each circuit element is adjusted such that clockwise currents flow in both in the first loop 421A and the second loop 421B at the time of signal reception, and a clockwise current flows in the first loop 421A and a counterclockwise current flows in the second loop 421B at the time of magnetic coupling, as illustrated in FIGS. 20(b) and 20(c), resulting in a butterfly current.

In this case, in the first loop 421A, the current mode at the time of magnetic coupling and the current mode at alone are almost in the same flow directions. Therefore, the first loop 421A is kept in the forward connection with the first low input impedance signal processing circuit 430A.

On the other hand, in the second loop 421B, the current mode at the time of magnetic coupling and the current mode at alone are in opposite directions. Therefore, the first loop 421B is backward-connected to the first low input impedance signal processing circuit 430B.

Here, a specific example of adjustment of the circuit element of this modification will be described. For example, a case where each circuit element is adjusted with the magnetic resonance frequency $f_0$ set to a nuclear magnetic resonance frequency of 124 MHz of hydrogen at a static magnetic field strength of 3 T (Tesla) will be described by way of an example.

As in the first embodiment, each circuit element is adjusted such that the equivalent circuits 605 and 606 illustrated respectively in FIGS. 20(b) and 20(c) resonate at 124 MHz and the impedance at both ends of the series circuit of the inductor 641A and the parallel capacitor 624A ($C_{14}$) becomes 50Ω. The value of the adjustment inductor 641 and the value of the parallel capacitor 624 are adjusted based on the characteristic principle of the parallel resonance circuit such that the above equations are satisfied and a flow of current at the time of coupling is in a desired form.

In the case of this modification, either the first sub-coil 410A or the second sub-coil 410B may be adjusted first.

When the value of a circuit element of one sub-coil 410 is adjusted, the resonance characteristic of the other sub-coil 410 is also affected. For this reason, the adjustment of the value of each circuit element of each sub-coil 410 is repeated several times to adjust the first sub-coil 410A and the second sub-coil 410B so as to resonate at 124 MHz.

When the value smaller than $f_0$ is 90 MHz, the values of the parameters adjusted by the above adjustment are, for example, $C_{11}$=7.7 pF, $C_{14}$=148 pF, $C_{21}$=98 pF, $C_{24}$=7.9 pF, $L_{12}$=11 nH and $L_{22}$=26 nH.

By performing the adjustment in this manner, the array coil 400 of this modification resonates at the nuclear magnetic resonance frequency and receives the nuclear magnetic resonance signal.

In addition, the first sub-coil 410A shares the second loop 421B to expand the sensitivity region and the second sub-coil 410B shares the first loop 421A to expand the sensitivity region.

In this manner, each of the sub-coils constituting the array coil 404 has sensitivity to a nuclear magnetic resonance signal to be received. At the same time, since the first sub-coil 410A is coupled to the second loop 421B by magnetic coupling, it may be regarded as a large coil loop and the sensitivity region is expanded. Specifically, since it has a sensitivity distribution like a butterfly coil, a deep sensitivity may be obtained. Likewise, since the second sub-coil 410B is coupled to the first loop 421A by magnetic coupling, it may be regarded as a large coil loop and the sensitivity region is expanded. Specifically, since it has a sensitivity distribution like a butterfly coil, the deep sensitivity may be obtained.

The sensitivity distributions of both sub-coils in an imaging region are different. Therefore, the array coil 404 of this modification operates as an array coil having a wide sensitivity range and high sensitivity without reducing the number of channels. Therefore, since the array coil 404 is a multi-channel coil having a wide sensitivity range, the array coil 404 of this modification is mutually magnetically coupled, thereby achieving both multi-channel and wide and deep sensitivity regions. In addition, since this is realized by the arrangement of each sub-coil 410 and the adjustment of the values of circuit elements, the structure is not complicated.

At the same time, by determining the circuit configuration of the low input impedance signal processing circuit 430 so that the phase difference of the generated rotating magnetic fields becomes 90 degrees or less, the two sub-coils may be tuned to enhance a signal and acquire the signal with high efficiency.

In the modification of the first embodiment, the same value (90 MHz) is used as the resonance frequency of the $L_{12}C_{14}$ resonance circuit and the $L_{22}C_{24}$ resonance circuit at the time of adjustment of each circuit element, but the present invention is not limited thereto. The resonance frequency may be different in each of the resonance circuits. By using different resonance frequency values for in each of the resonance circuits, since a current flowing to a magnetic coupling destination is changed, it is possible to design a sensitivity region that is suitable for the purpose. The magnitude of the difference between the resonance frequency of these resonance circuits and $f_0$ is not particularly limited. However, the difference of the resonance frequency of the $L_{22}C_{24}$ resonance circuit from $f_0$ is preferably 10% or more.

In the first embodiment, it is illustrated the case where an array coil 700 having a coil with the magnetic coupling adjustment circuit satisfying the equation (9), which intentionally generates the magnetic coupling, is used, but the present invention is not limited thereto. Any combination of coils may be used as long as it satisfies the equation (10). Even for magnetic coupling inevitably caused by the shape and size of the coil loop, by configuring the circuit so that the phase difference between rotating magnetic fields generated in the region of interest by a current flowing through each coil is less than 90 degrees, a signal in the region of interest may be detected with high efficiency to improve the sensitivity.

Second Embodiment

Next, a second embodiment of the present invention will be described. In the first embodiment, an array coil is formed by combining two sub-coils. In the second embodiment, an example in which three or more sub-coils are combined to form an array coil to realize multi-channel and wide sensitivity regions and high sensitivity is illustrated. By using a plurality of coils, the sensitivity may be improved.

An MRI apparatus of the second embodiment basically has the same configuration as the MRI apparatus 100 of the first embodiment. Hereinafter, the second embodiment will be described focusing on a configuration different from that of the first embodiment.

Figure 21:
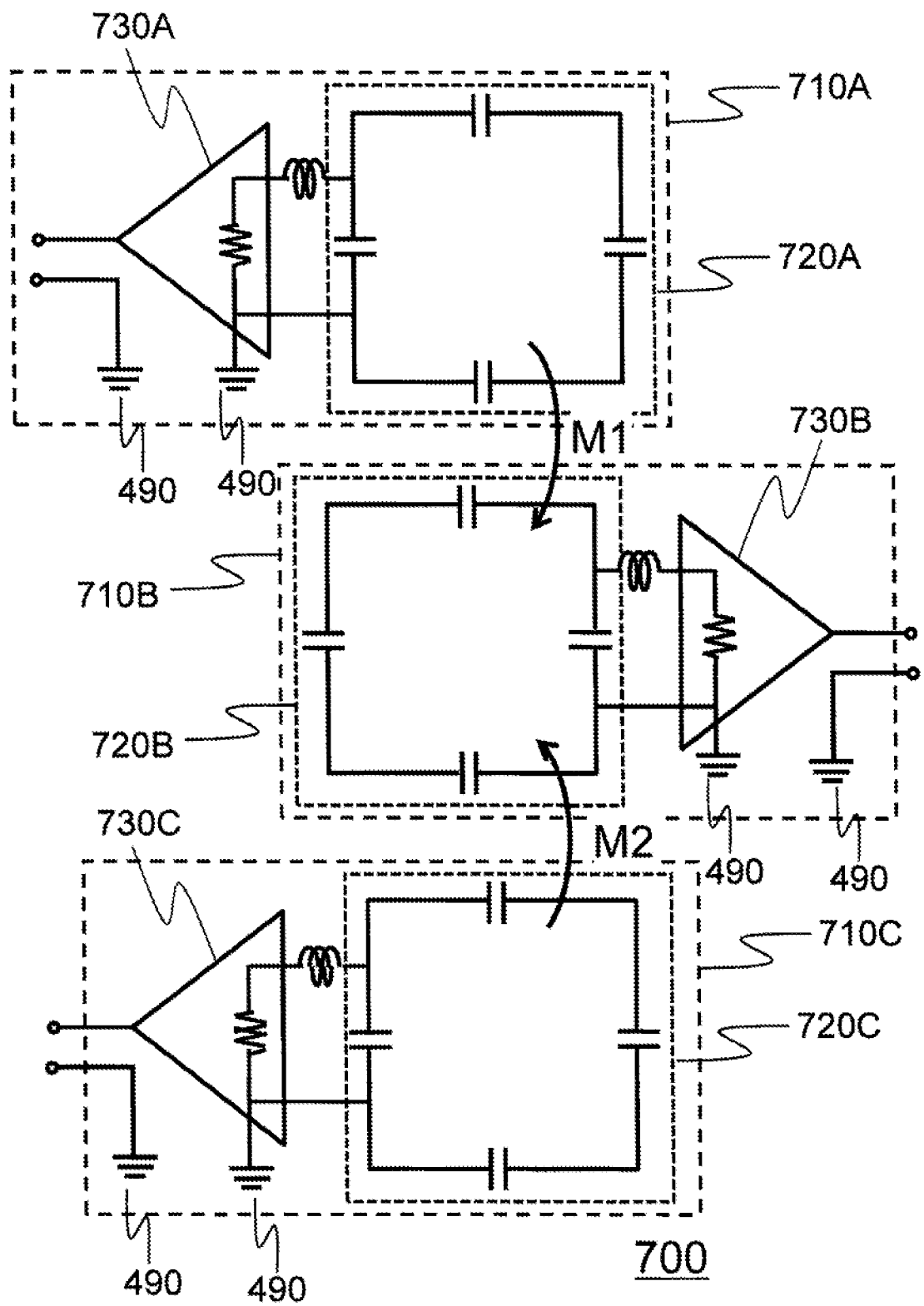
FIG. 21 is an explanatory view for explaining an array coil according to a second embodiment.

FIG. 21 is a view for explaining an array coil 700 of the second embodiment. As illustrated in this figure, the array coil 700 of the second embodiment includes a first sub-coil 710A, a second sub-coil 710B and a third sub-coil 710C.

These coils are arranged in this order at positions at which adjacent channels (sub-coils 710) may be magnetically coupled.

The first sub-coil 710A and the third sub-coil 710C have the same configuration as the first sub-coil 410A of the first embodiment. The second sub-coil 710B is the same as the second sub-coil 410B of the first embodiment. Respective capacitor and inductor are adjusted to satisfy the equations (7) to (10), as in the first embodiment.

That is, an RF coil (array coil 700) of the second embodiment includes a third sub-coil 710C having a third loop coil part 720A and capable of transmitting/receiving a nuclear magnetic resonance signal, in addition to the first sub-coil 710A and the second sub-coil 710B.

In the second embodiment also, as in the first embodiment, a loop coil part 720B of the second sub-coil 710B and a loop coil part 720C of the third sub-coil 710C are adjusted to be magnetically coupled, and are respectively arranged at positions at which an RF magnetic field generated in a space formed between the second sub-coil 710B and the third sub-coil 710C may be detected as the RF signal.

Furthermore, the third sub-coil 710C alone has a resonance frequency different from the nuclear magnetic resonance frequency. The third sub-coil 710C is adjusted such that, when it is magnetically coupled to the second sub-coil 710B, a circulating current path is formed in a loop of the third loop coil part 720C and a loop of the second loop coil part 720B and the third sub-coil 710C resonates at the nuclear magnetic resonance frequency.

First, each of the sub-coils 710A, 710B and 710C of the second embodiment is adjusted to resonate at the nuclear magnetic resonance frequency of atoms of a detection target. For example, it is adjusted to resonate at the nuclear magnetic resonance frequency of 124 MHz of hydrogen at a static magnetic field strength of 3 T (Tesla). Each circuit element of the second sub-coil 710B is adjusted so that the $L_{22}C_{23}$ resonance circuit does not resonate at the nuclear magnetic resonance frequency. That is, it is adjusted so as not to have high resistance when receiving a signal of this frequency. In addition, the first sub-coil 710A and the third sub-coil 710C are adjusted such that the $L_{12}C_{14}$ resonance circuit resonates at the nuclear magnetic resonance frequency and has high resistance when receiving a signal of this frequency.

The loop coil part 720A of the first sub-coil 710A is magnetically coupled with the loop coil part 720B of the second sub-coil 710B at the time of signal reception. This is because the first sub-coil 710A and the second sub-coil 710B are arranged at positions at which they can be magnetically coupled and each circuit element of the second sub-coil 710B is adjusted according to the above-mentioned equation (9) so as not to have high resistance at the time of signal reception (magnetic coupling removal is not applied). In this case, the magnitude of mutual inductance between the first sub-coil 710A and the second sub-coil 710B is assumed as M1.

In the meantime, the first loop coil part 720A is hardly magnetically coupled to the loop coil part 720C of the third sub-coil 710C, and vice versa. This is because the both loop coil parts are spaced apart from each other and the $L_{12}C_{14}$ resonance circuit resonates at the nuclear magnetic resonance frequency to have high resistance when receiving a signal of this frequency.

Similarly, the third loop coil part 720C is magnetically coupled to the second loop coil part 720B at the time of signal reception. This is because the third sub-coil 710C and the second sub-coil 710B are arranged at positions at which they can be magnetically coupled and each circuit element of the second sub-coil 710B is adjusted according to the above-mentioned equation (9) so as not to have high resistance at the time of signal reception (magnetic coupling removal is not applied). In this case, the magnitude of mutual inductance between the third sub-coil 710C and the second sub-coil 710B is assumed as M2.

Further, the second loop coil part 720B is magnetically coupled to neither the first loop coil part 720A nor the third loop coil part 720C at the time of signal reception. This is because both of the first sub-coil 710A and the third sub-coil 710C have high resistance at the time of signal reception as their respective circuit elements are adjusted according to the above equation (10).

Therefore, at the time of signal reception, the first sub-coil 710A of the array coil 700 of the second embodiment effectively forms a current path like a butterfly coil as the first loop coil part 720A is magnetically coupled to the second loop coil part 720B. Since the second sub-coil 710B is not magnetically coupled to any other sub-coils at the time of signal reception, it has a general surface coil current path. The third sub-coil 710C effectively forms a current path like a butterfly coil at the time of signal reception when the third loop coil part 720C is magnetically coupled to the second loop coil part 720B.

Accordingly, each sub-coil 710 resonates at the nuclear magnetic resonance frequency of the detection target. In addition, the first sub-coil 710A and the third sub-coil 710C are magnetically coupled to the second sub-coil 710B at the time of signal reception to effectively form a current path like a butterfly coil. Therefore, they have a wide and deep sensitivity region. In the meantime, the second sub-coil 710B is not magnetically coupled to the other sub-coils 710 at the time of signal reception. Therefore, the sub-coils 710 exhibit different sensitivity distributions for a imaging region.

Even in the second embodiment, in one sub-coil 710, the loop 721 and a low input impedance signal processing circuit 730 are connected such that the phase difference between rotating magnetic fields generated at magnetic coupling and at alone is less than 90 degrees.

That is, in each of the second sub-coil 710C and the third sub-coil 10C, the loop coil unit 720 and the signal processing circuit 730 are connected such that the phase difference between a second rotating magnetic field generated in the region of interest of the subject by the loop coil part 720 alone and a third rotating magnetic field generated in the region of interest of the subject by magnetic coupling of the loop coil part 720 is less than 90 degrees.

In this manner, in the array coil 700 of the second embodiment, the low input impedance signal processing circuit 730 is connected such that the phase difference of the rotating magnetic fields generated in the region of interest of the subject becomes 90 degrees or less. Therefore, when a magnetic coupling occurs, a current flowing in one sub-coil 710 is not canceled out due to the influence of a current flowing to another adjacent sub-coil 710. There is no change in sensitivity due to an unexpected rotating magnetic field. Therefore, with the array coil 700 of the second embodiment, similarly to the first embodiment, a plurality of sub-coils may be tuned to enhance a signal and receive the signal efficiently with high sensitivity.

Therefore, the array coil 700 of the present embodiment realizes a wide sensitivity region, high sensitivity, and multi-channel.

<Modification: Number of Sub-Coils>

In the second embodiment, the case of combining three sub-coils 710A, 710B, and 710C has been described by way of an example. However, the number of sub-coils 710 is not limited thereto but may be four or more. By increasing the number of sub-coils 710, it is possible to provide sensitivity in a wider region.

<Modification: Magnetic Coupling Pattern>

In the second embodiment, at the time of signal reception, each circuit element is adjusted such that the first sub-coil 710A is coupled to the second sub-coil 710B, the third sub-coil 710C is coupled to the second sub-coil 710B, and the second sub-coil 710B is coupled to neither the first sub-coil 710A nor the third sub-coil 710C.

However, the pattern of magnetic coupling is not limited to this configuration. For example, each circuit element may be adjusted such that each of the first sub-coil 710A and the second sub-coil 710B is magnetically coupled to the third sub-coil 710C, and the third sub-coil 710C is not coupled to any sub-coil. In addition, each circuit element may be adjusted such that each of the second sub-coil 710B and the third sub-coil 710C is magnetically coupled to the first sub-coil 710A, and the first sub-coil 710A is not coupled to any sub-coil.

Further, each circuit element may be adjusted such that the first sub-coil 710A is coupled to the second sub-coil 710B, the second sub-coil 710B is coupled to the third sub-coil 710C, and the third sub-coil 710C is coupled to neither. In this case, a magnetic coupling removing unit may be provided to remove magnetic coupling by overlapping a portion of the loop coil parts 720 to prevent the third sub-coil 710C from being magnetically coupled to the first sub-coil 710A and the second sub-coil 710B. The degree of freedom in designing a sensitivity region is improved since different sensitivity distribution from the present embodiment can be realized.

Furthermore, a case where each circuit element is adjusted to produce magnetic coupling in one direction has been described by way of an example, the present invention is not limited thereto. Similarly to the modification of the first embodiment, each circuit element may be adjusted such that the second sub-coil 710B is also be magnetically coupled to the first and third sub-coils 710A and 710C.

Regardless of the coupling mode, the array coil 700 of the second embodiment and the array coil of the modification thereof may operate as an array coil having a wide sensitivity range without reducing the number of channels. In addition, since this is realized by the arrangement of each sub-coil 710 and the value of the circuit element thereof, the structure is not complicated. Therefore, with the array coil 700 of the second embodiment, it is possible to achieve both multi-channel and wide and deep sensitivity region with a simple configuration. In addition, by using the array coil 700 as the receiving RF coil 161, the MRI apparatus of the second embodiment may obtain a high quality image at a high speed.

In the second embodiment, since a combination of the sub-coils to be magnetically coupled can be freely selected, various sensitivity distributions may be realized by selection. Therefore, the degree of freedom in designing a sensitivity region is improved.

Further, the modifications of the first embodiment for the type of circuit element used for the low input impedance signal processing circuit, the resonance frequency used for circuit element adjustment, the arrangement position of each sub-coil, the presence or absence of a coupling inductor, the loop shape, the size of each sub-coil, etc. are also applicable to the second embodiment.

Even in the second embodiment, as in the first embodiment, on the contrary, it is not necessary to intentionally cause magnetic coupling between the sub-coils 710.

<Modification of Sub-Coil Arrangement>

In each of the above-described embodiments, the respective sub-coils 410 and 710 (hereinafter represented by the reference numeral of the first embodiment) are arranged in substantially the same plane without overlapping. However, the arrangement of each sub-coil 410 is not limited thereto. It is sufficient if the sub-coil 410 can be arranged at a position at which a rotating magnetic field generated in a space between adjacent sub-coils 410 is detectable as the RF signal.

For example, the adjacent sub-coils 410 may be partially overlapped to prevent magnetic coupling between the sub-coils 410.

Figure 22A:
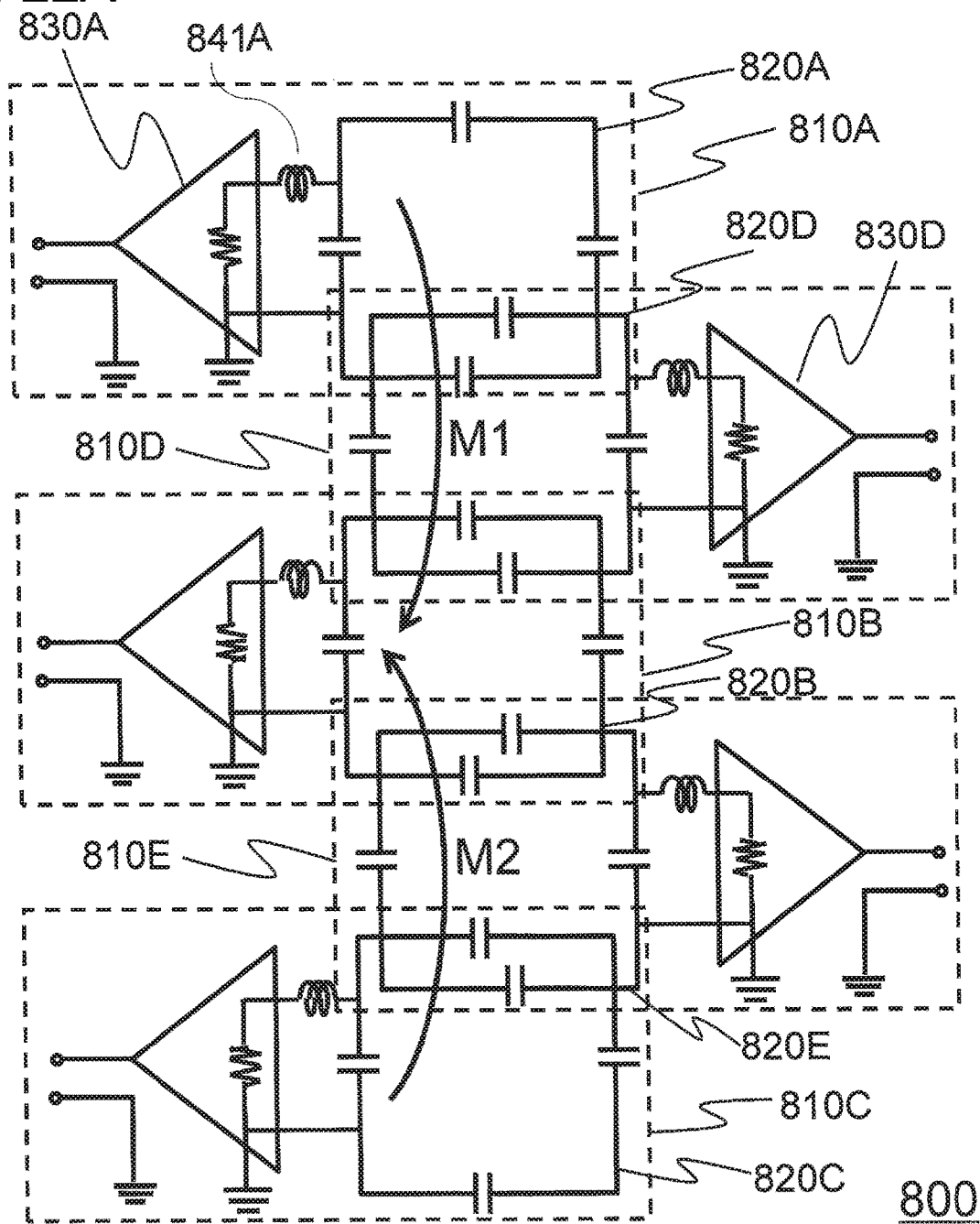
FIGS. 22A and 22B are explanatory views for explaining an array coil according to a modification of the first and second embodiments.
Figure 22B:
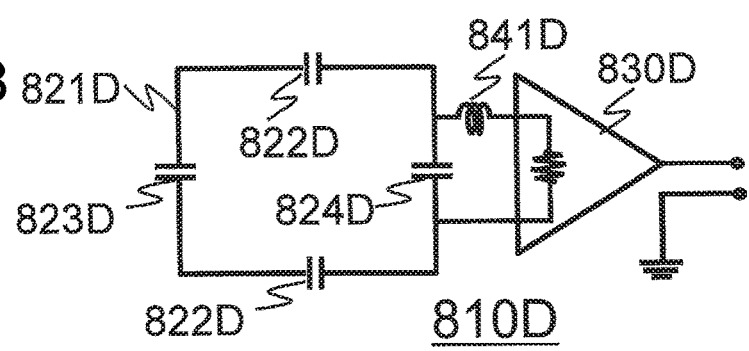

An example of an array coil 800 in this case is illustrated in FIGS. 22(*a*) and 22(*b*). Here, a case where the array coil 800 is composed of five sub-coils 810 will be described by way of an example. However, the number of sub-coils 810 constituting the array coil 800 is not limited thereto.

The first sub-coil 810A, the fourth sub-coil 810D, the second sub-coil 810B, the fifth sub-coil 810E, and the third sub-coil 810C are arranged in order from the top.

Each sub-coil 810 has the same configuration as the sub-coil 410 of the first embodiment. That is, each sub-coil 810 further includes a first magnetic coupling adjusting part 841 connecting a loop coil part 820 and a first low input impedance signal processing circuit 830 to which the sub-coil 810 is connected, and the first loop coil part 820 includes a first series capacitor 822 inserted in series with the inductor component of a loop 821 and a first series capacitor 824 inserted in parallel to the inductor component to make the first loop coil part 820 a parallel resonance circuit.

As illustrated in these figures, each sub-coil 810 is arranged so that the adjacent sub-coil 810 overlaps a portion of the loop 821 of the loop coil part 820. At this time, the overlap amount is determined so that magnetic coupling between the adjacent sub-coils 810 is removed. That is, the adjacent sub-coils 810 are overlapped so as to remove the magnetic coupling.

That is, in the array coil 800 of the second embodiment, for example, the fourth loop coil part 820D is arranged so as to have an overlap region with each of the first loop coil part 820A and the second loop coil part 820B. The area of the overlap region is determined such that the fourth sub-coil 810D is not magnetically coupled to the first sub-coil 810A and the second sub-coil 810B.

Likewise, the fifth loop coil part 820E is arranged so as to have an overlap region with the second loop coil part 820B and the third loop coil part 820C. The area of the overlap region is determined such that the fifth sub-coil 810E is not magnetically coupled to the second sub-coil 810B and the third sub-coil 810C.

[Adjustment of Circuit Element]

Basically, the respective circuit elements of the first sub-coil 810A, the second sub-coil 810B and the third sub-coil 810C are adjusted in the same manner as the modification of the second embodiment in which each sub-coil 810 is magnetically coupled to an adjacent sub-coil at the time of signal reception. Hereinafter, the adjustment of each circuit element of the fourth sub-coil 810D and the fifth sub-coil 810E will be described with reference to FIG. 22(*b*) by way of an example of the fourth sub-coil 810D.

The values of series capacitors 822D ($C_{12}$) and 823D ($C_{13}$) are adjusted so that a circuit excluding the low input impedance signal processing circuit 830D from the fourth sub-coil 810D resonates at the nuclear magnetic resonance frequency $f_0$ (124 MHz in the case of hydrogen) of a detection target and the impedance at both ends of a series circuit of the inductor 641A and the parallel capacitor 624A ($C_{14}$) becomes 50Ω. In addition, an adjustment inductor 841D ($L_{22}$) is adjusted such that a circuit excluding the loop of the loop coil part 820D has high impedance at $f_0$ (124 MHz in the case of hydrogen).

Each circuit element of the fifth sub-coil 810E is also adjusted in the same manner.

[Connection]

Further, as in the above-described embodiments, in each sub-coil 810, the loop coil part 820 and the low input impedance signal processing circuit 830 are connected such that the phase difference between the first rotating magnetic field generated in the region of interest of the subject by the loop coil part 820 alone and the second rotating magnetic field generated in the region of interest of the subject by magnetic coupling of the loop coil part 820 is less than 90 degrees.

In the array coil 800 of this modification, each circuit element is adjusted as described above. As a result, in addition to the operation of the second embodiment, the fourth sub-coil 810D and the fifth sub-coil 810E arranged therebetween resonate at 124 MHz to acquire a nuclear magnetic resonance signal.

In addition, in the array coil 800 of this modification, each loop coil part 820 and the low input impedance signal processing circuit 830 are connected as described above. Therefore, a signal detected alone is not weakened due to a signal generated by the magnetic coupling. Therefore, a nuclear magnetic resonance signal may be acquired with high efficiency.

In this manner, according to this modification, in addition to the effects of the second embodiment, since more coils can be arranged, the sensitivity may be improved. In addition, the degree of freedom in design of a sensitivity region is increased to improve the sensitivity.

Further, in this modification, the case where five sub-coils 810 are provided has been described by way of an example, but the number of sub-coils is not limited thereto.

For example, three of the first sub-coil 810A, the second sub-coil 810B and the fourth sub-coil 810D may be used. In this case, the first sub-coil 810A and the second sub-coil 810B are adjusted in the same manner as the sub-coil 410 of the first embodiment.

Even in this modification, the magnetic coupling patterns of the first sub-coil 810A, the second sub-coil 810B and the third sub-coil 810C are not limited to the above example. Other various patterns similar to those of the second embodiment may be applied.

Further, the modifications of the first embodiment for the type of circuit element used for the low input impedance signal processing circuit 830, the resonance frequency used for circuit element adjustment, the arrangement position of each sub-coil 810, the presence or absence of a coupling inductor, the loop shape, the size of each sub-coil 810, etc. are also applicable to this modification.

<Modification of Applicable MRI Apparatus>

In each of the above-described embodiments, the present invention is applied to the MRI apparatus 100 including the horizontal magnetic field type magnet 110, but it is also applicable to an MRI apparatus 101 of a vertical magnetic field type as described above. That is, even in the vertical magnetic field type MRI apparatus 101, it is possible to use a multi-channel array coil (for example, the array coil 800 illustrated in FIGS. 22(a) and 22(b)) using a plurality of surface coils, which have been conventionally difficult to use. Therefore, even in the vertical magnetic field type MRI apparatus 101, the degree of freedom of the design of the array coil may be increased to improve the sensitivity. Moreover, as the degree of freedom is increased, it is also possible to simplify the array coil, allowing a design in a lightweight array coil. Accordingly, the burdens on the operator and the subject may be reduced.

REFERENCE SIGNS LIST

090: coordinate system, 100: MRI apparatus, 101: MRI apparatus, 102: table, 103: subject, 110: magnet, 111: magnet, 121: shim coil, 122: shim power supply, 131: gradient magnetic field coil, 132: gradient magnetic field power supply, 140: sequencer, 151: transmitting RF coil, 152: RF magnetic field generator, 161: receiving RF coil, 162: receiver, 170: computer, 171: display device, 180: magnetic coupling prevention circuit driver, 210: transmission-reception magnetic coupling prevention circuit, 211: PIN diode, 212: control signal line: 220: transmission-reception magnetic coupling prevention circuit, 220m: transmission-reception magnetic coupling prevention circuit, 221: PIN diode, 221m: cross diode, 222: inductor, 223: control signal line, 300: birdcage-shaped RF coil, 301: straight conductor, 302: end conductor, 303: capacitor, 311: input port, 312: input port, 400: array coil, 401: array coil, 402: saddle type array coil, 403: solenoid type array coil, 404: array coil, 405: butterfly type array coil, 410: sub-coil, 410A: first sub-coil, 410B: second sub-coil, 420: loop coil part, 420A: first loop coil part, 420B: second loop coil part, 421: loop, 421A: first loop, 421B: second loop, 422: series capacitor, 422A: first series capacitor, 422B: second series capacitor, 423: capacitor, 424: parallel capacitor, 424A: first parallel capacitor, 424B: second parallel capacitor, 430: low input impedance signal processing circuit, 430A: first low input impedance signal processing circuit, 430B: second low input impedance signal processing circuit, 431: low input impedance signal amplifier, 431A: first low input impedance signal amplifier, 431B: second low input impedance signal amplifier, 441: magnetic coupling adjusting part (adjustment inductor), 441A: first magnetic coupling adjusting part, 441B: second magnetic coupling adjusting part, 451: coupling inductor, 451A: first coupling inductor, 451B: second coupling inductor, 462: loop, 462A: first loop, 462B: second loop, 463A: first loop, 463B: second loop, 465A: first loop, 465B: second loop, 471: current mode, 472: current mode, 490: earth (ground), 500: parallel resonance circuit, 501: capacitor, 502: inductor, 521: solid line, 522: broken line, 600: equivalent circuit, 601: equivalent circuit, 602: equivalent circuit, 604: equivalent circuit, 605: equivalent circuit, 606: equivalent circuit, 621: inductor, 621A: first inductor, 621B: second inductor, 622: series capacitor, 622A: first series capacitor, 622B: second series capacitor, 624: parallel capacitor, 624: parallel capacitor, 624A: first parallel capacitor, 624B: second parallel capacitor, 626A: first inductor, 626B: second inductor, 627: inductor, 632A: first impedance, 632B: second impedance, 641: adjustment inductor, 641A: first adjustment inductor, 641B: second adjustment inductor, 700: array coil, 710: sub-coil, 710A: first sub-coil, 710B: second sub-coil, 710C: third sub-coil, 720: loop coil part, 720A: first loop coil part, 720B: second loop coil part, 720C: third loop coil part, 730: low input impedance signal processing circuit, 800: array coil, 810: sub-coil, 810A: first sub-coil, 810B: second sub-coil, 810C: third sub-coil, 810D: fourth sub-coil, 810E: fifth sub-coil, 820: loop coil part, 820A: first loop coil part, 820B: second loop coil part, 820C: third loop coil part, 820D: fourth loop coil part, 820E: fifth loop coil part, 821: loop, 822: series capacitor, 822D: fourth series capacitor, 824: parallel capacitor, 830: low input impedance signal processing circuit, 830D: fourth low input impedance signal processing circuit, 841: magnetic coupling adjusting part, 841D: fourth magnetic coupling adjusting part (adjustment inductor)

The invention claimed is:

1. A radio frequency coil comprising:
a first sub-coil and a second sub-coil, each of which includes a loop coil part that is formed of a conductor and detects a radio frequency signal and a signal processing circuit to which the radio frequency signal detected by the loop coil part is input,
wherein the loop coil part of the first sub-coil and the loop coil part of the second sub-coil are adjusted to be magnetically coupled to each other and are respectively arranged at positions at which a radio frequency magnetic field generated in a space between the first sub-coil and the second sub-coil is detectable as the radio frequency signal, and
the loop coil part and the signal processing circuit are connected such that a phase difference between a rotating magnetic field generated by a first radio frequency magnetic field generated in the space by the loop coil part alone and a rotating magnetic field formed by a second radio frequency magnetic field generated in the space by magnetic coupling of the loop coil part is less than 90 degrees, in each of the first sub-coil and the second sub-coil.

2. The radio frequency coil according to claim 1, wherein one terminal of an output side of the signal processing circuit is grounded, and
the loop coil part is a parallel resonance circuit.

3. The radio frequency coil according to claim 1, wherein a resonance frequency of the first sub-coil alone is different from a reception frequency which is a frequency of the radio frequency signal to be received, and the first sub-coil is arranged and adjusted such that a circulating current path is formed in each of a loop of the loop coil part of the first sub-coil and a loop of the loop coil part of the second sub-coil by being magnetically coupled to the second sub-coil, and the first sub-coil resonates at the reception frequency.

4. The radio frequency coil according to claim 3, wherein the resonance frequency of the second sub-coil alone is different from the reception frequency, and the second sub-coil is adjusted such that a circulating current path is formed in each of the loop of the loop coil part of the first sub-coil and the loop of the loop coil part of the second sub-coil by being magnetically coupled to the first sub-coil, and the second sub-coil resonates at the reception frequency.

5. The radio frequency coil according to claim 3, wherein each of the first sub-coil and the second sub-coil includes a magnetic coupling adjusting part that connects the loop coil part and the signal processing circuit,
the loop coil part includes:
a series capacitor inserted in series with an inductor component of the loop; and
a parallel capacitor inserted in parallel with the inductor component to make the loop coil part a parallel resonance circuit,
the magnetic coupling adjusting part includes at least one of a capacitor and an inductor as an adjustment circuit element, and
the first sub-coil and the second sub-coil are tuned by the adjustment circuit element, the series capacitor and the parallel capacitor.

6. The radio frequency coil according to claim 3, wherein each of the first sub-coil and the second sub-coil further includes a coupling inductor, and
the first sub-coil and the second sub-coil are magnetically coupled by the respective coupling inductors.

7. The radio frequency coil according to claim 1, wherein the first sub-coil and the second sub-coil are arranged in substantially a same plane.

8. The radio frequency coil according to claim 1, further comprising a third sub-coil including the loop coil part and the signal processing circuit,
wherein the loop coil part of the second sub-coil and the loop coil part of the third sub-coil are adjusted so as to be magnetically coupled to each other and are respectively arranged at positions at which a radio frequency magnetic field generated in a space between the second sub-coil and the third sub-coil is detectable as the radio frequency signal, and
the loop coil part and the signal processing circuit are connected such that a phase difference between a rotating magnetic field generated by a second radio frequency magnetic field generated in the space by the loop coil part alone and a rotating magnetic field formed by a third radio frequency magnetic field generated in the space by magnetic coupling of the loop coil part is less than 90 degrees, in each of the third sub-coil and the second sub-coil.

9. The radio frequency coil according to claim 8, wherein a resonance frequency of the third sub-coil alone is different from a frequency of the radio frequency signal, and the third sub-coil is arranged and adjusted such that a circulating current path is formed in each of a loop of the loop coil part of the third sub-coil and a loop of the loop coil part of the second sub-coil by being magnetically coupled to the second sub-coil, and the third sub-coil resonates at the frequency of the radio frequency signal.

10. The radio frequency coil according to claim 8, further comprising a fourth sub-coil including the loop coil part and the signal processing circuit,
wherein the fourth sub-coil is arranged such that the loop coil part of the fourth sub-coil has an overlap region with each of the loop coil part of the first sub-coil and the loop coil part of the second sub-coil, and
the area of the overlap region is determined such that the fourth sub-coil is not magnetically coupled to the first sub-coil and the second sub-coil.

11. A magnetic resonance imaging apparatus comprising:
a static magnetic field forming unit that forms a static magnetic field;
a gradient magnetic field forming unit that forms a gradient magnetic field;
a radio frequency magnetic field generating unit that generates a radio frequency magnetic field;
a transmitting coil that irradiates a subject with the radio frequency magnetic field;
a receiving coil that detects a nuclear magnetic resonance signal, which is a radio frequency signal, from the subject; and
an image reconstructing unit that reconstructs an image from the detected nuclear magnetic resonance signal, wherein the receiving coil is a radio frequency coil according to claim 1, and each of the transmitting coil and the receiving coil includes a magnetic coupling prevention circuit that prevents magnetic coupling between the transmitting coil and the receiving coil.

\* \* \* \* \*